(12) United States Patent
Zhang et al.

(10) Patent No.: US 12,017,369 B2
(45) Date of Patent: Jun. 25, 2024

(54) NULL SPACE CONTROL FOR END EFFECTOR JOINTS OF A ROBOTIC INSTRUMENT

(71) Applicant: Verb Surgical Inc., Santa Clara, CA (US)

(72) Inventors: Xiaobin Zhang, Santa Clara, CA (US); Dimitri Chatzigeorgiou, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 928 days.

(21) Appl. No.: 17/063,309

(22) Filed: Oct. 5, 2020

(65) Prior Publication Data

US 2022/0105639 A1    Apr. 7, 2022

(51) Int. Cl.
    *B25J 9/16*     (2006.01)
    *A61B 17/072*   (2006.01)
    (Continued)

(52) U.S. Cl.
    CPC .......... *B25J 9/1689* (2013.01); *A61B 34/25* (2016.02); *A61B 34/35* (2016.02); *A61B 34/37* (2016.02);
    (Continued)

(58) Field of Classification Search
    CPC ........ B25J 9/1689; B25J 9/1643; B25J 13/06; A61B 34/25; A61B 34/35; A61B 34/37;
    (Continued)

(56) References Cited

U.S. PATENT DOCUMENTS 6,981,628 B2    1/2006  Wales
8,245,898 B2    8/2012  Smith
(Continued)

FOREIGN PATENT DOCUMENTS

KR   20140113209 A    9/2014
WO   2014146113 A1    9/2014
WO   2016152046 A1    9/2016

OTHER PUBLICATIONS

International Search Report and Written Opinion for International Patent Application No. PCT/IB2021/059042 dated Dec. 30, 2021.
(Continued)

*Primary Examiner* — Abby Y Lin
*Assistant Examiner* — Danielle M Jackson
(74) *Attorney, Agent, or Firm* — Lempia Summerfield Katz LLC

(57) ABSTRACT

The disclosed embodiments relate to systems and methods for a surgical tool or a surgical robotic system. One example method includes providing a redundant degree of freedom (DoF) for an end effector joint of one DoF by driving the joint with two actuators, calculating a position displacement of the joint to effect a desired end effector movement in response to an input command, calculating a first movement of the two actuators based on the position displacement of the joint and a second movement of the two actuators based on a second control objective in a null space corresponding to the redundant DoF, and driving the joint according to the first movement and the second movement to effect the desired end effector movement while accomplishing the second control objective in the null space.

19 Claims, 16 Drawing Sheets

(51) Int. Cl.
*A61B 17/29* (2006.01)
*A61B 34/00* (2016.01)
*A61B 34/35* (2016.01)
*A61B 34/37* (2016.01)
*A61B 90/00* (2016.01)
*B25J 13/06* (2006.01)

(52) U.S. Cl.
CPC ............. *A61B 34/71* (2016.02); *B25J 9/1643* (2013.01); *B25J 13/06* (2013.01); *A61B 17/072* (2013.01); *A61B 2017/07285* (2013.01); *A61B 17/29* (2013.01); *A61B 2034/715* (2016.02); *A61B 2034/742* (2016.02); *A61B 2034/743* (2016.02); *A61B 2034/744* (2016.02); *A61B 2090/066* (2016.02); *A61B 90/37* (2016.02)

(58) Field of Classification Search
CPC ....... A61B 34/71; A61B 17/072; A61B 17/29; A61B 90/37; A61B 2017/07285; A61B 2034/715; A61B 2034/742; A61B 2034/743; A61B 2034/744; A61B 2090/066; A61B 34/30; A61B 2034/2059; A61B 90/06; G05B 2219/39457; G05B 2219/40236
See application file for complete search history.

(56) References Cited

U.S. PATENT DOCUMENTS

| | | | |
|---|---|---|---|
| 8,306,656 B1* | 11/2012 | Schaible | A61B 34/71 700/245 |
| 9,439,649 B2 | 9/2016 | Shelton, IV | |
| 2010/0152898 A1* | 6/2010 | Reiland | B25J 9/1633 700/261 |
| 2011/0282491 A1* | 11/2011 | Prisco | A61B 34/30 700/258 |
| 2012/0123441 A1* | 5/2012 | Au | A61B 34/30 606/130 |
| 2012/0158017 A1 | 6/2012 | Naylor et al. | |
| 2014/0081461 A1 | 3/2014 | Williamson et al. | |
| 2016/0221189 A1* | 8/2016 | Nilsson | B25J 9/1653 |
| 2019/0000576 A1* | 1/2019 | Mintz | A61B 34/25 |
| 2019/0193278 A1* | 6/2019 | Larose | B25J 13/025 |
| 2020/0275984 A1* | 9/2020 | Brisson | A61B 34/71 |
| 2021/0402603 A1* | 12/2021 | Murphy | A61B 34/37 |
| 2023/0404376 A1* | 12/2023 | Diolaiti | A61B 90/37 |

OTHER PUBLICATIONS

Petrović, Petar B., Nikola Lukić, and Ivan Danilov. "Compliant behaviour of redundant robot arm-experiments with null-space." Serbian Journal of Electrical Engineering 12.1 (2015): 81-98.

* cited by examiner

NULL SPACE CONTROL FOR END EFFECTOR JOINTS OF A ROBOTIC INSTRUMENT

FIELD

This disclosure relates to control of a surgical robotic tool with one or more actuators.

BACKGROUND

Surgical robotic systems give an operator or user, such as an operating surgeon, the ability to perform one or more actions of a surgical procedure. In the surgical robotic system, a surgical tool or instrument, such as an endoscope, clamps, cutting tools, spreaders, needles, energy emitters, etc., is mechanically coupled to a robot joint, so that movement or actuation of the robot joint directly causes a rotation, pivoting, or linear movement of a part of the tool. Once the tool is attached to (e.g., in contact with) a tool driver in the arm, operator commands may cause movements and activate functions of the attached tool.

Robot joints are driven in a variety of techniques. In many examples, each degree of freedom corresponds to a joint and corresponding actuator and motor. Some joints are directly driven by a drive train such that a single motor drives the joint in two directions. In this example, there is a direct correlation between motor position and joint position. For any given motor position, there is only one corresponding joint position.

Other drive techniques may involve multiple motors to drive a joint. In this example, the motors may cooperate to provide a certain joint position. That is, there are multiple possible positions for the two motors that cooperate to provide the desired joint position. Additional benefits may be realized by selecting from among the multiple possible motor positions.

SUMMARY

Disclosed herein is a robotically-assisted surgical electromechanical system designed for surgeons to perform minimally-invasive surgery. A suite of compatible tools can be attached/detached from an instrument driver mounted to the distal end of a robotic arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints.

One example robotic method includes providing a redundant degree of freedom (DoF) for an end effector joint of one DoF by driving the joint with two actuators, calculating a position displacement of the joint to effect a desired end effector movement in response to an input command, calculating a first movement of the two actuators based on the position displacement of the joint and a second movement of the two actuators based on a second control objective in a null space corresponding to the redundant DoF, and driving the joint according to the first movement and the second movement to effect the desired end effector movement while accomplishing the second control objective in the null space.

One example apparatus to provide a control objective using a null space of a redundant degree of freedom of a surgical tool includes a tool driver including a plurality of actuators providing a redundant degree of freedom (DoF) for an end effector joint of one DoF and one or more processors. The one or more processors are configured to provide a redundant degree of freedom (DoF) for an end effector joint of one DoF by driving the joint with two actuators, calculate a position displacement of the joint to effect a desired end effector movement in response to an input command, calculate a first movement of the two actuators based on the position displacement of the joint and a second movement of the two actuators based on a second control objective in a null space corresponding to the redundant DoF, and generate a joint command for the joint according to the first movement and the second movement to effect the desired end effector movement while accomplishing the second control objective in the null space.

One example non-transitory computer readable medium including instructions to cause one or more processors to perform identifying a redundant degree of freedom (DoF) for an end effector joint of one DoF by driving the joint with a plurality of actuators, calculating a position displacement of the joint to effect a desired end effector movement in response to an input command, calculating a first movement of the two actuators based on the position displacement of the joint and a second movement of the two actuators based on a second control objective in a null space corresponding to the redundant DoF, and driving the joint according to the first movement and the second movement to effect the desired end effector movement while accomplishing the second control objective in the null space.

DETAILED DESCRIPTION

Figure 1:
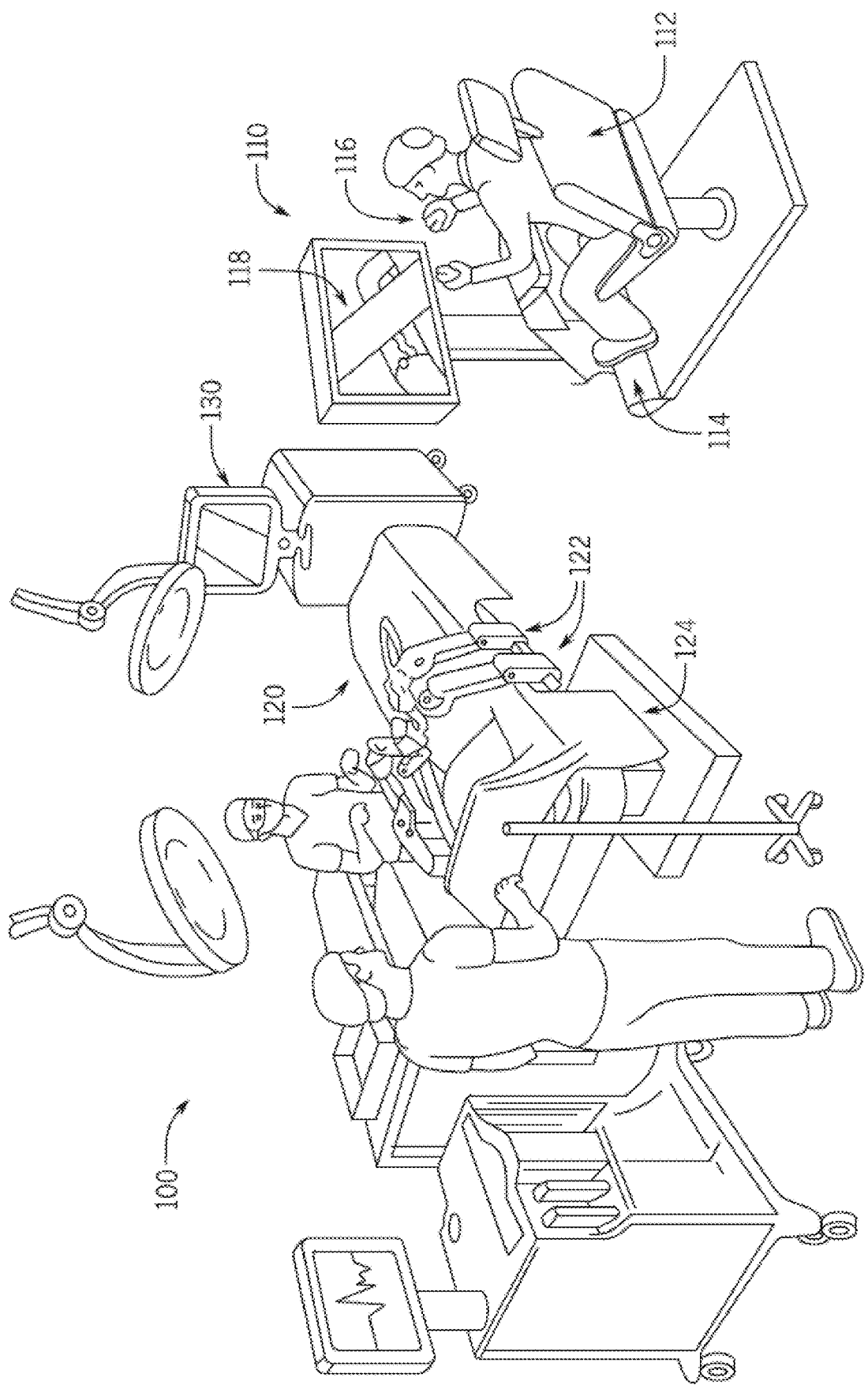
FIG. 1 illustrates an example operating room environment including a surgical robotic system.

The following embodiments relate to control systems for an endoscopic surgical instrument. Endoscopic surgical instruments typically include a long, thin tube that is inserted directly into the body to observe or otherwise perform a task on an internal organ or tissue. Endoscopic surgical instruments may be inserted through an incision or other opening of the body such as the mouth or anus. Endoscopic surgical instruments may be suitable for precise placement of a distal end effector at a desired surgical site through a cannula. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, radio frequency (RF) treatment, lasers, or others).

As discussed in more detail below, the endoscopic instrument may include multiple joints, with at least one joint having a redundant degree of freedom. The redundant degree of freedom means that the number of motors or actuators for the joint is greater than the number of axes for the joint. In most scenarios, the number of axes for a joint is one. For a joint without a redundant degree of freedom, there may be a direct (1:1) relationship or other linear relationship between the motor position and the joint position. However, for a joint with a redundant degree of freedom, there is more than one position for the motors or actuators that provides any given joint position.

A relationship for positions of the motors or actuators and the joint position may be described algebraically. A solution of the relationship is provided by the null space. The null space defines the possibilities for the positions of the motors or actuators while still maintaining the desired joint position. Within this null space, the positions of the motors or actuators can be changed to optimize another control objective. The following control systems select positions of the motors or actuators within the null space so that both the desired position of the joint and at least one additional control objective is achieved.

For example, the following embodiments described apparatus and methods for null space control for a surgical tool's articulation joint and/or closure joint. In the case of the articulation joint, a minimum amount of tension is maintained for the articulation motors to prevent slack in the joint motion and maintain a prescribed level of pre-tension throughout the total use of the surgical instrument. Thus, the additional control objective achieved is the prescribed level of pre-tension. The prescribed level of pre-tension is maintained while also providing the desired joint position.

In the case of the closure joint, the system guarantees two closure motors could help each other to deliver large amount of required joint level torque. Thus, the additional control objective achieved is the large amount of joint torque. The joint torque is maintained while also providing the desired joint position.

FIG. 1 is a diagram illustrating an example operating room environment with a surgical robotic system 100. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. The robotic arms 122 are shown as table-mounted, but other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or teleoperated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic-assisted minimally invasive surgery (MIS) and manual laparoscopic surgery on a patient.

An end effector may be configured to execute a surgical operation such as cutting, grasping, poking, or energy emission. The surgical tool may be manipulated manually, robotically, or both, during the surgery. For example, the surgical tool may be a tool used to enter, view, or manipulate an internal anatomy of the patient. In an embodiment, the surgical tool is a grasper that can grasp tissue of the patient. The surgical tool may be controlled manually, directly by a hand of a bedside operator or it may be controlled robotically, via sending electronic commands to actuate movement.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues, or performing manual repositioning or tool exchange involving one or more robotic arms 122. Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The surgical platform 124 and robotic arms 122 may be in a fully-stowed configuration with the arms 122 under the surgical platform 124 for storage and/or transportation purposes. The surgical team can extend the arms from their stowed position for sterile draping.

After draping, the arms 122 can be partially retracted until needed for use. A number of conventional laparoscopic steps may be performed including trocar placement and installation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars.

After insufflation, if required, manual instruments can be inserted through the sleeve to perform any laparoscopic steps by hand. Next, the surgical team may position the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The surgical platform 124 can be repositioned intraoperatively. For safety reasons, all tooltips should be in view and under active control by the surgeon at the user console 110. Instruments that are not under active surgeon control are removed, and the table feet are locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

Figure 2:
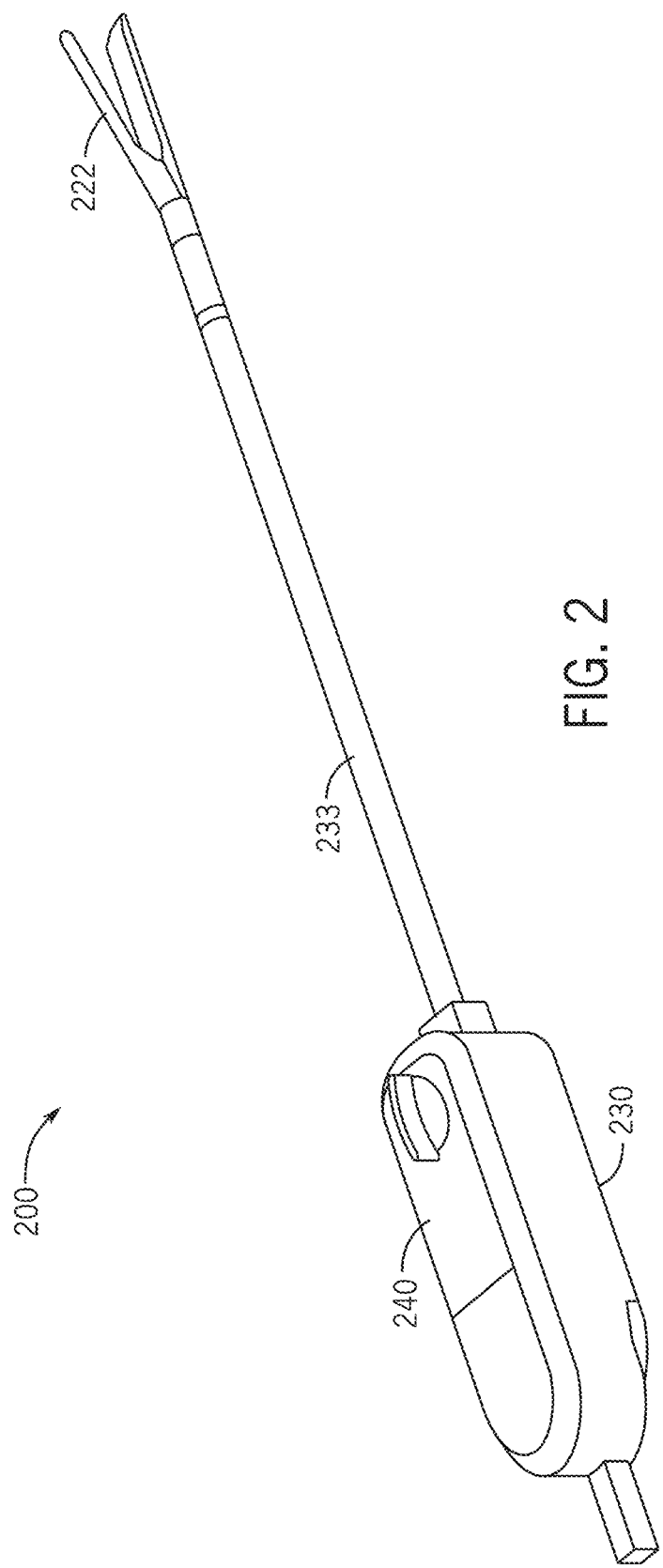
FIG. 2 illustrates an example surgical tool.

FIG. 2 illustrates an example surgical tool assembly 200. The surgical tool assembly 200 includes a surgical tool 240 to a tool driver 230. The surgical tool 240 is connected to end effector 222 via shaft 233. Additional, different, or fewer components may be included.

The surgical tool assembly 200 may be an endoscopic surgical instrument. The surgical tool assembly 200 may be an endocutter. An endocutter may be configured to divide and seal tissue. Put another way, an endocutter may be configured to cut and staple tissue with motion provided by an articulation joint. The endocutter may be used to cut and staple tissue in a variety of surgical procedures, including bariatric, thoracic, colorectal, gynecologic, urologic, and general surgery. Common clinical use scenarios include reshaping organs, the removal or repair of organs, tissue fixation, dissection, or the creation of anastomoses (or any combination of these). FIG. 2 is an illustration of a subsystem or a part of the surgical robotic system 100, for detecting engagement of a surgical tool 240 to a tool driver 230 of a surgical robotic arm 122. The surgical robotic arm 122 may be one of the surgical robotic arms of surgical robotic system 100 illustrated and discussed with respect to FIG. 1. The control unit 210 may be part of for example the control tower in FIG. 1. As discussed in more detail herein, the engagement may be detected by control unit 210 based on one or more rotary motor operating parameters of one or more actuators (e.g., actuator 238-$j$) in the tool driver 230.

There is a tool driver 230 to which different surgical tools (e.g., surgical tool 240, as well as other detachable surgical tools for rotation of an endoscope camera, pivoting of a grasper jaw, or translation of a needle) may be selectively attached (one at a time.) This may be done by for example a human user holding the housing of the surgical tool 240 in her hand and moving the latter in the direction of arrow 280 shown until the outside surface of the surgical tool 240 in which there are one or more tool disks (e.g., tool disk 244-$i$ described below) comes into contact with the outside surface of the tool driver 230 in which there are one or more drive disks (e.g., drive disk 234-$j$ described below). The one or more tool disks and/or one or more drive disks may be implemented by pucks, which may be formed of plastic or another durable material. In the example shown, the tool driver 230 is a segment of the surgical robotic arm 122 at a distal end portion of the surgical robotic arm 122. A proximal end portion of the arm is secured to a surgical robotic platform, such as a surgical table that shown in FIG. 1 described above.

The control system is described in detail with respect to FIG. 12 below. By of introduction to the control system, the control system of FIG. 12 includes a control unit 210 configured to control motion of the various motorized joints in the surgical robotic arm 122 (including the drive disks 234) through which operation of end effector 222 (its position and orientation as well as its surgical function such as opening, closing, cutting, applying pressure, etc.) which mimics that of a user input device is achieved. This is achieved via a mechanical transmission in the surgical tool 240, when the surgical tool 240 has been engaged to transfer force or torque from the tool driver 230. The control unit 210 may be implemented as a programmed processor, for example as part of the control tower 130 of FIG. 1. It may respond to one or more user commands received via a local or remote user input (e.g., joystick, touch control, wearable device, or other user input device communicating via a console computer system.) Alternatively, the control unit 210 may respond to one or more autonomous commands or controls (e.g., received form a trained surgical machine learning model that is being executed by the control unit 210 or by the console computer system), or a combination thereof. The commands dictate the movement of robotic arm 122 and operation of its attached end effector 222.

An end effector 222 may be any surgical instruments, such as jaws, a cutting tool, an endoscope, spreader, implant tool, stapler, etc. FIG. 2 includes an endocutter having a combination of two or more of these instruments such as a cutting tool, jaws, and stapler. Different surgical tools each having different end effectors can be selectively attached (one at a time) to robotic arm 122 for use during a surgical or other medical procedure.

The robotic arm includes a tool driver 230, in which there are one or more actuators, such as actuator 238-j. Each actuator may be a linear or rotary actuator that has one or more respective electric motors (e.g., a brushless permanent magnet motor) whose drive shaft may be coupled to a respective drive disk 234-j through a transmission (e.g., a gear train that achieves a given gear reduction ratio). The tool driver 230 includes one or more drive disks 234 that may be arranged on a planar or flat surface of the tool driver 230, wherein the figure shows several such drive disks that are arranged on the same plane of the flat surface. Each drive disk (e.g., drive disk 234-j) is exposed on the outside surface of the tool driver 230 and is designed to mechanically engage (e.g., to securely fasten via snap, friction, or other mating features) a mating tool disk 244-j of the surgical tool 240, to enable direct torque transfer between the two. This may take place once for example a planar or flat surface of the surgical tool 240 and corresponding or mating planar or flat surface of the tool driver 230 are brought in contact with one another.

Furthermore, a motor driver circuit (for example, installed in the tool driver 230 or elsewhere in the surgical robotic arm 122) is electrically coupled to the input drive terminals of a constituent motor of one or more of the actuators 238. The motor driver circuit manipulates the electrical power drawn by the motor in order to regulate for example the speed of the motor or its torque, in accordance with a motor driver circuit input, which can be set or controlled by control unit 210, which results in the powered rotation of the associated drive disk (e.g., drive disk 234-j).

When the mating drive disk 234-j is mechanically engaged to a respective tool disk 244-j, the powered rotation of the drive disk 234-j causes the tool disk 244-j to rotate, e.g., the two disks may rotate as one, thereby imparting motion on, for example, linkages, gears, cables, chains, or other transmission devices within the surgical tool 240 for controlling the movement and operation of the end effector 222 which may be mechanically coupled to the transmission device.

Different surgical tools may have different numbers of tool disks based on the types of movements and the number of degrees of freedom in which the movements are performed by their end effectors, such as rotation, articulation, opening, closing, extension, retraction, applying pressure, etc.

Furthermore, within the surgical tool 240, more than one tool disk 244 may contribute to a single motion of the end effector 222 to achieve goals such as load sharing by two or more motors that are driving the mating drive disks 234, respectively. In another aspect, within the tool driver 230, there may be two or more motors whose drive shafts are coupled (via a transmission) to rotate the same output shaft (or drive disk 234), to share a load.

In yet another aspect, within the surgical tool 240, there may be a transmission which translates torque from two drive disks 234 (via respective tool disks 244) for performing complementary actions in the same degree of freedom, e.g., a first drive disk 234-j rotates a drum within the housing of the surgical tool 240 to take in one end of a rod, and a second drive disk 234-i rotates another drum within the housing of the surgical tool 240 to take in the other end of the rod. As another example, the extension and the shortening of an end effector along a single axis may be achieved using two tool disks 234-i, 234-j, one to perform the extension and another to perform the retraction. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 222 being jaws, two or more tool disks 244 may cooperatively control the motion of the jaws, for load sharing, as discussed in greater detail herein.

In yet another aspect, within the surgical tool 240, there may be a transmission which translates torque from two drive disks 234 (via respective tool disks 244) for performing complimentary actions in the same degree of freedom, e.g., a first drive disk 234-i rotates a drum within the housing of the surgical tool 240 to take in one end of a cable, and a second drive disk 234-j rotates another drum within the housing of the surgical tool 240 to take in the other end of the cable. As another example, the extension and the shortening of an end effector along a single axis may be achieved using two tool disks 234-i, 234-j, one to perform the extension and another to perform the retraction, for example via different cables. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 246 being jaws, two or more tool disks 244 may cooperatively control the motion of the jaws, for load sharing, as discussed in greater detail herein.

Figure 3:
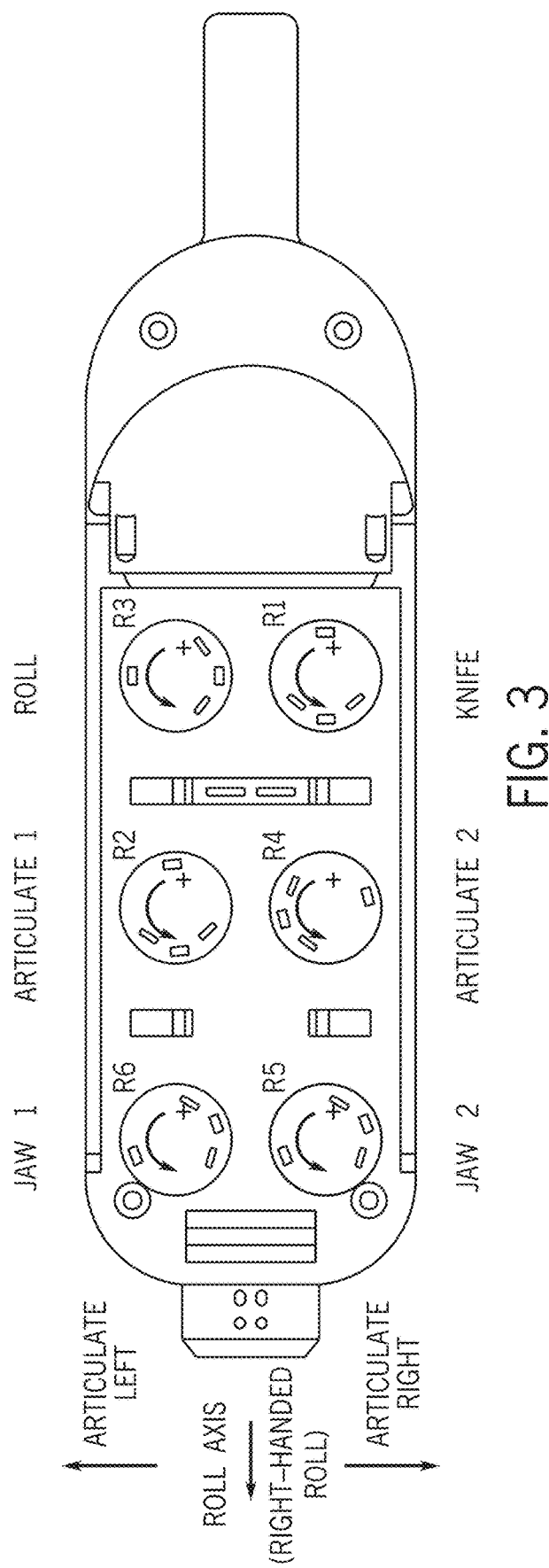
FIG. 3 illustrates a mapping for the tool driver to the surgical tool.

FIG. 3 illustrates a mapping for the tool driver 230 to the surgical tool 240. FIG. 3 illustrates rotary device assignments or mapping for tool disks R1-R6. In this example, tool disk R1 is assigned to a cutting instrument such as a knife. As the tool disk R1 is moved in one direction (e.g., clockwise) the cutting instrument advances, and as the tool disk R1 is moved in a second direction (e.g., counterclockwise) the cutting blade retracts.

Tool disks R2 and R4 are assigned to the articulation joint. The tool disks R2 and R4 may be connected to the end effector 222 in an antagonistic pairs, that is, when one cable of the antagonistic pair is actuated or tensioned, while the other cable is loosened, the jaw will rotate in one direction. When only the other cable is tensioned, the jaw will rotate in an opposite direction. One direction (e.g., clockwise) corresponds to articulation of the end effector 222 to the left, and the other direction (e.g., counterclockwise) corresponds to the articulation of the end effector to the right. Articulation may be a change in orientation of the end effector 222 at an axis transverse to the longitudinal axis of the shaft of the instrument. This articulated positioning permits the clinician to more easily engage tissue in some instances. In addition, articulated positioning advantageously allows an endoscope to be positioned behind the end effector without being blocked by the instrument shaft.

Tool disk R3 is mapped to the roll axis of the end effector. The tool disk R3 may be coupled to one or more gears that drive the wrist to rotate about the roll axis. The rotation of the tool disk R1 in a first direction with respect to the plane of the tool disks (e.g., clockwise) may cause rotation of the roll axis of the end effector in the same direction (e.g., clockwise) and rotation of the tool disk R1 in a second direction with respect to the plane of the tool disks (e.g., counter clockwise) may cause rotation of the roll axis of the end effector in the same direction (e.g., counter clockwise).

Tool disks R5 and R6 are assigned to the closure device or jaw. For example, the one of the opposing jaws may be assigned to tool disk R5 and tool disk R6 operation in one direction for opening the jaw (i.e., increasing the angle between the opposing jaws) and another direction for closing the jaw (i.e., decreasing the angle between the opposing jaws).

In some embodiments, when surgical tool 240 is first attached to or installed on tool driver 230 such that the tool disks are brought substantially into coplanar and coaxial alignment with corresponding drive disks (though the tool and drive disks are perhaps not yet successfully engaged), control unit 210 initially detects the type of the surgical tool 240. In one embodiment, surgical tool 240 has an information storage unit 242, such as a solid state memory, radio frequency identification (RFID) tag, bar code (including two-dimensional or matrix barcodes), etc., that identifies its tool or end effector information, such as one or more of identification of tool or end effector type, unique tool or end effector ID, number of tool disks used, location of those tool disks being used (e.g., from a total of six possible tool disks 244-e, f, g, h, i, j), type of transmission for the tool disks (e.g., direct drive, cable driven, etc.), what motion or actuation a tool disk imparts on the end effector, one or more tool calibration values (e.g., a rotational position of the tool disk as determined during factor testing/assembly of the tool), whether motion of the end effector is constrained by a maximum or minimum movement, as well as other tool attributes. In one embodiment, the information storage unit 242 identifies minimal information, such as a tool ID, which control unit 210 may use to perform a lookup of the various tool attributes.

The tool driver 230 may include a communication interface 232 (e.g., a memory writer, a near field communications, near field communication (NFC), transceiver, RFID scanner, barcode reader, etc.) to read the information from the information storage unit 242 and pass the information to control unit 210. Furthermore, in some embodiments, there may be more than one information storage unit in surgical tool 240, such as one information storage unit associated with each tool disk 244. In this embodiment, tool driver 230 may also include a corresponding sensor for each possible information storage unit that would be present in a given tool.

After surgical tool 240 is attached with tool driver 230, such that tool disks are brought into alignment and are superimposed on corresponding drive disks (although not necessarily mechanically engaged), and after the tool disk information is obtained, e.g., read by control unit 210, the control unit 210 performs an engagement process to detect when all of the tool disks that are expected to be attached to respective drive disks are mechanically engaged with their respective drive disks (e.g., their mechanical engagement has been achieved, or the tool driver 230 is now deemed engaged with the tool). That is, attaching the surgical tool 240 with the tool driver 230 does not necessarily ensure the proper mating needed for mechanical engagement of tool disks with corresponding drive disks (e.g., due to misalignment of mating features). The engagement process may include activating one or more motors of an actuator (e.g., actuator 238-$j$) that drives a corresponding drive disk 234-$j$. Then, based on one or more monitored motor operating parameters of the actuator 238-$j$, while the latter is driving the drive disk 234-$j$, the mechanical engagement of the tool disk 244-$i$ with a drive disk 234-$j$ can be detected. This process may be repeated for every drive disk 234 (of the tool driver 230) that is expected to be currently attached to a respective tool disk 244 (e.g., as determined based on the tool disk information obtained for the particular surgical tool 240 that is currently attached.)

Upon detecting that a particular type of surgical tool 240 has been attached with the tool driver 230, the control unit 210 activates one or more actuators (e.g., motors) of the tool driver 230 that have been previously associated with that type of surgical tool 240. In some embodiments, each actuator that is associated with a corresponding drive disk 234 of surgical tool 240 may be activated simultaneously, serially, or a combination of simultaneous and serial activation.

Figure 4:
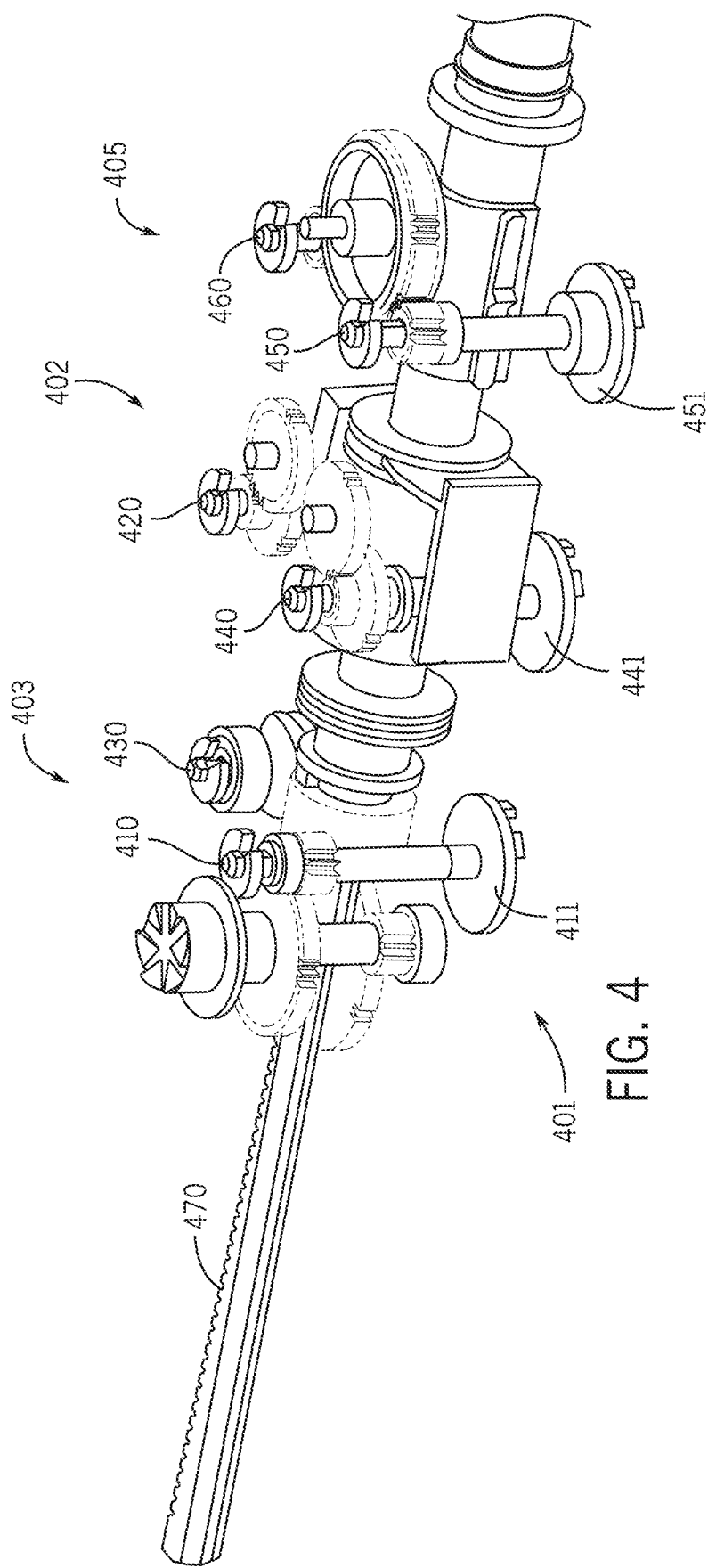
FIG. 4 illustrates a view of a drive system for the surgical tool.
Figure 5:
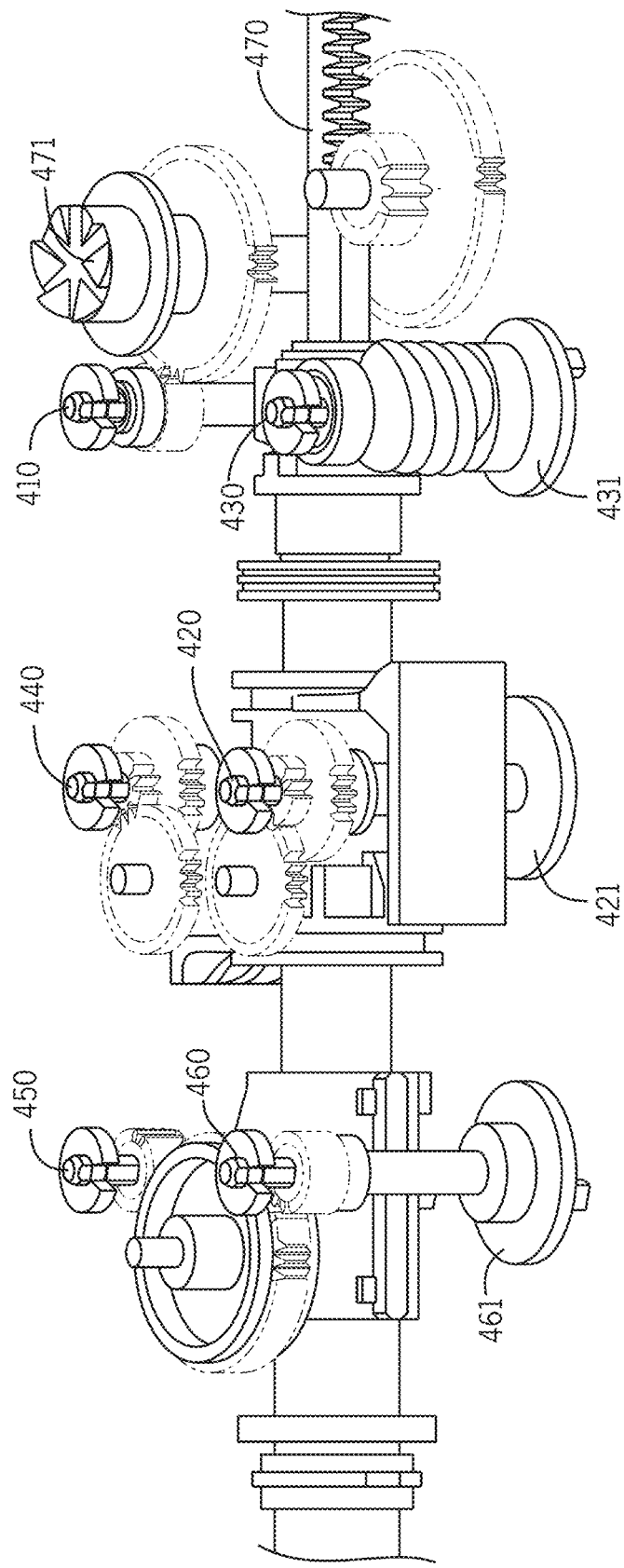
FIG. 5 illustrates another view of a drive system for the surgical tool.

FIGS. 4-11 illustrate a drive system for the surgical tool 240. FIG. 4 illustrates a left side view of a drive system for the surgical tool and FIG. 5 illustrates a right side view of the drive system. The drive system includes a fire subsystem 401, an articulation subsystem 402, a roll subsystem 403, and a closure subsystem 405. Additional, different, or fewer components may be included.

Figure 6:
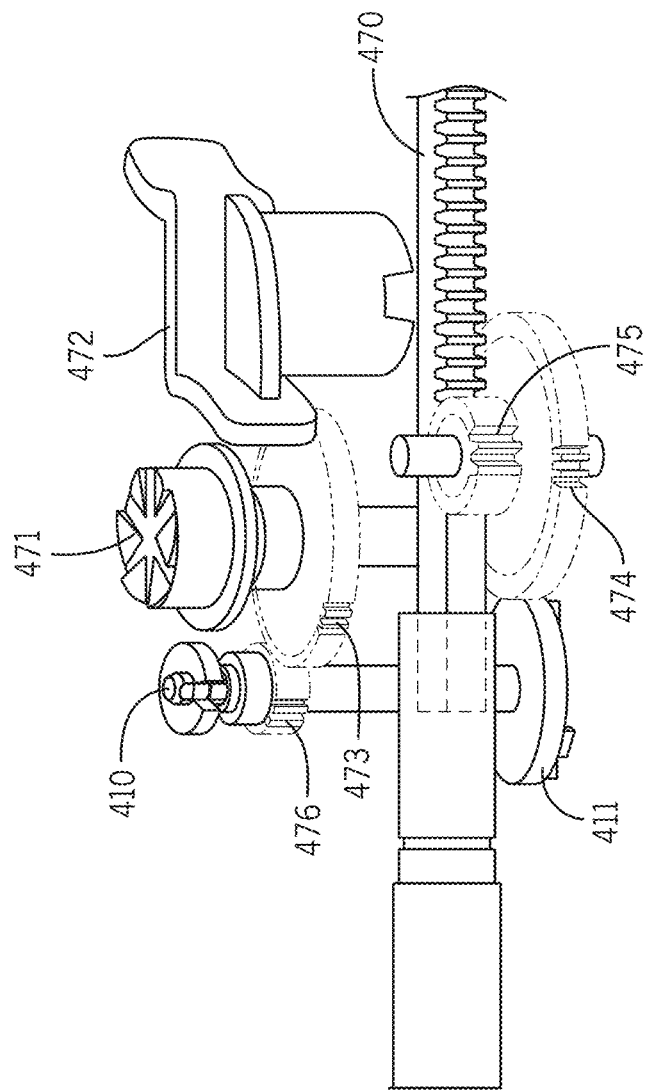
FIG. 6 illustrates a firing subsystem of the drive system for the surgical tool.

FIG. 6 illustrates the firing subsystem 401 of the drive system for the surgical tool. The fire subsystem 401 includes a firing shaft 410 that is rigidly connected to tool disk R1 (firing input puck 411). The firing shaft 410 may be coupled to and support the firing input puck 411 such that the firing input puck 411 is mounted to the firing shaft 410. Also mounted to the firing shaft 410 may be a driving gear 476 (firing shaft driving gear). The driving gear 476 imparts motion and torque onto driven gear 473. The driven gear 473 is part of the drive train to the drive bar 470 and also facilitates the bailout mechanism. The rest of the drive train to the drive bar 470 includes a gear reduction set including gear 474 driven by the shaft of the driven gear 473 and a pinion gear 475 that runs along the rack of the drive bar 470.

The bailout mechanism includes a manual bailout input cylinder 471. The user input device 472 fits over the manual bailout input cylinder 471, or is otherwise coupled to the manual bailout input cylinder 471. Rotating the manual bailout input cylinder 471 through user input a portion of the drive train out of engagement with the drive bar 470. This manually overrides the movement of the drive bar 470 from the tool driver 230.

Figure 7:
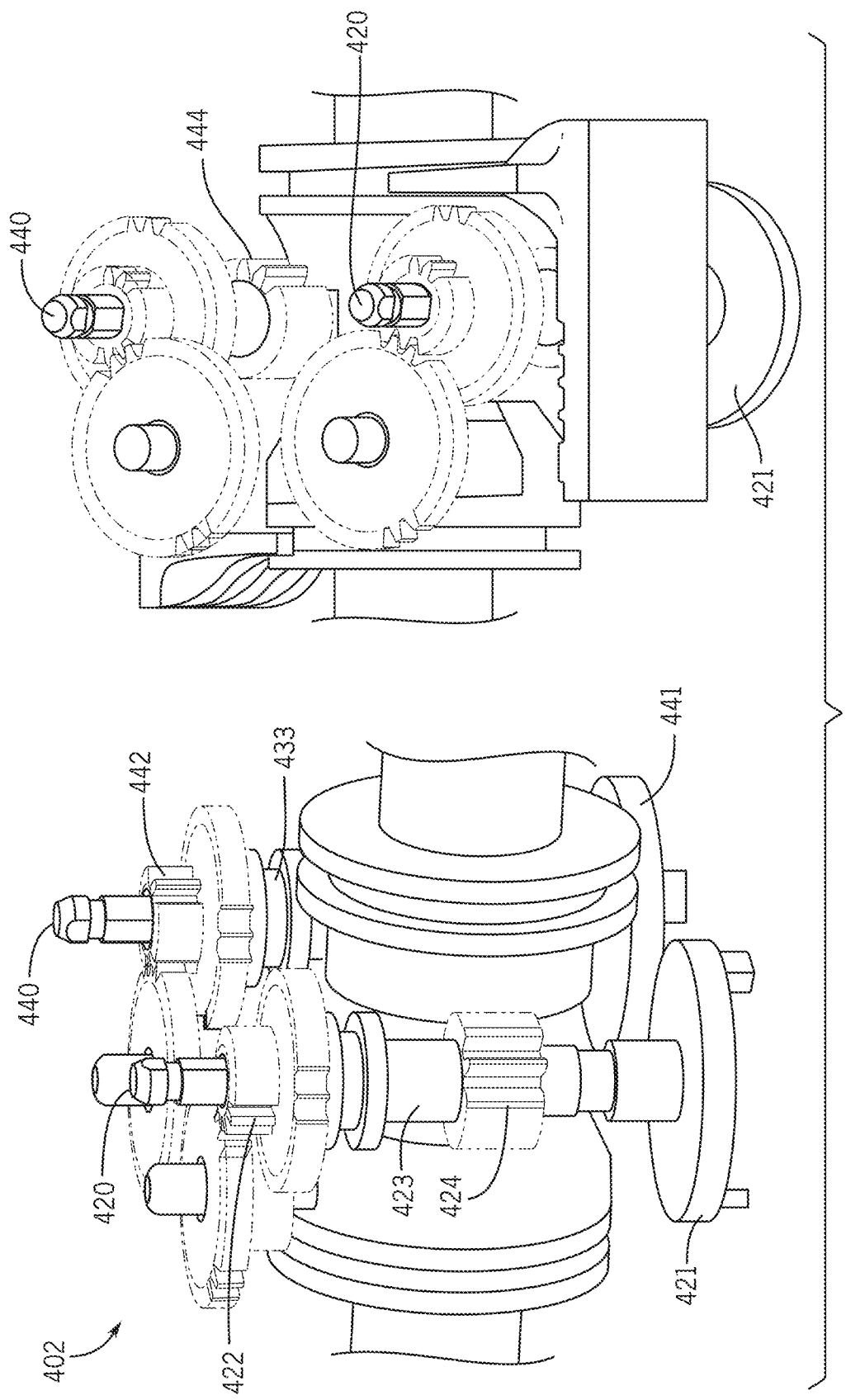
FIG. 7 illustrates an articulation subsystem of the drive system for the surgical tool.
Figure 8:
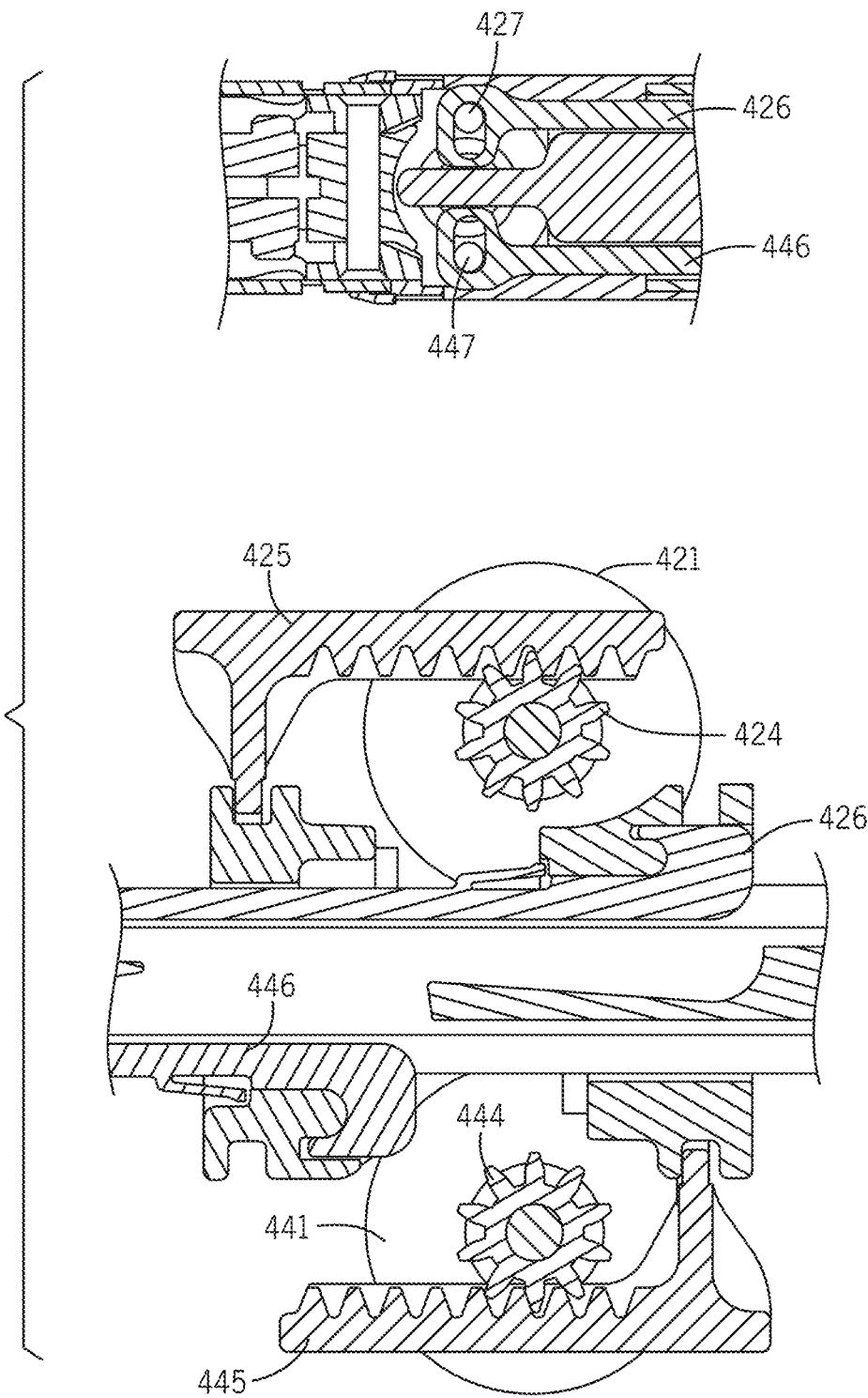
FIG. 8 illustrates a top down view of the articulation subsystem.

FIG. 7 illustrates the articulation subsystem 402 of the drive system for the surgical tool. FIG. 8 illustrates a top down view of the articulation subsystem 402. The articulation subsystem 402 includes a left articulation shaft 440 and a right articulation shaft 420. The left articulation shaft 440 is coupled to and driven by tool disk R4 (left articulation input puck 441). The right articulation shaft 420 is coupled to and driven by tool disk R2 (right articulation input puck 421). The left articulation shaft 440 includes a left pinion gear 444 connected to the articulation joint. The right articulation shaft 420 includes a right pinion gear 420 connected to the articulation joint.

FIG. 8 provides more detail of the drive of the articulation joint. Right pinion gear 424 drives right rack 425 connected to the articulation joint. Left pinion gear 444 drives left rack 445 connection to the articulation joint. The right rack 425 (e.g., first rigid rod) moves the right articulation arm 426 and ultimately causes the right protrusion 427 of the articulation joint to rotate about the center of the articulation disk. Likewise, the left rack 445 (e.g., second rigid rod) moves the left articulation arm 446 and ultimately causes the left protrusion 447 of the articulation joint to rotate about the center of the articulation disk. Movement of the right rack 425 and/or the left rack 445 applies torques at the wrist to create articulation movement.

Figure 9:
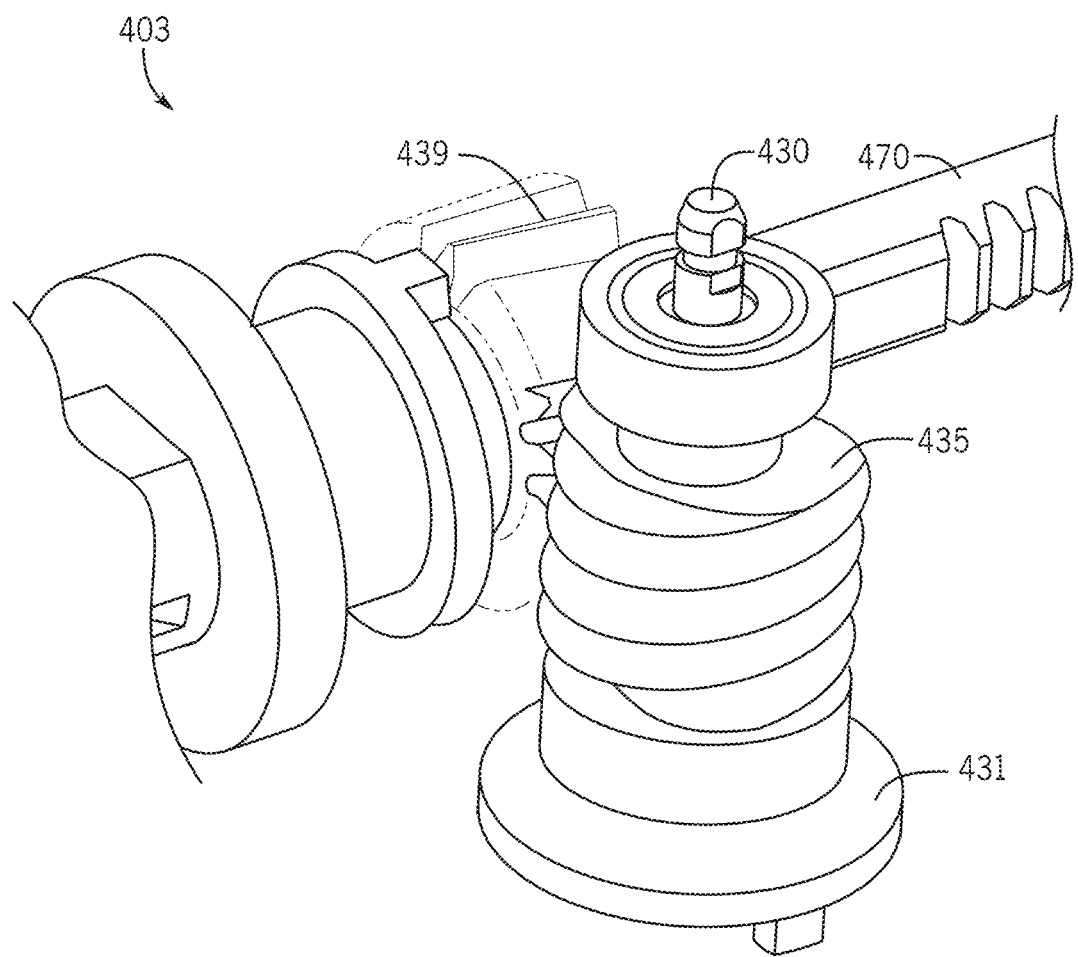
FIG. 9 illustrates a roll subsystem of the drive system for the surgical tool.

FIG. 9 illustrates the roll subsystem 403 of the drive system for the surgical tool. The roll subsystem 403 includes a roll shaft 430. The roll shaft 430 is coupled to and driven by tool disk R3 (roll input puck 431). The roll input puck 431 is coupled to the roll shaft 430 along with worm gear 435 in order to drive roll gear 439. The roll gear 439 provides the motion to the roll joint in either the clockwise or counterclockwise direction depending on the rotation of the tool disk R3.

Figure 10:
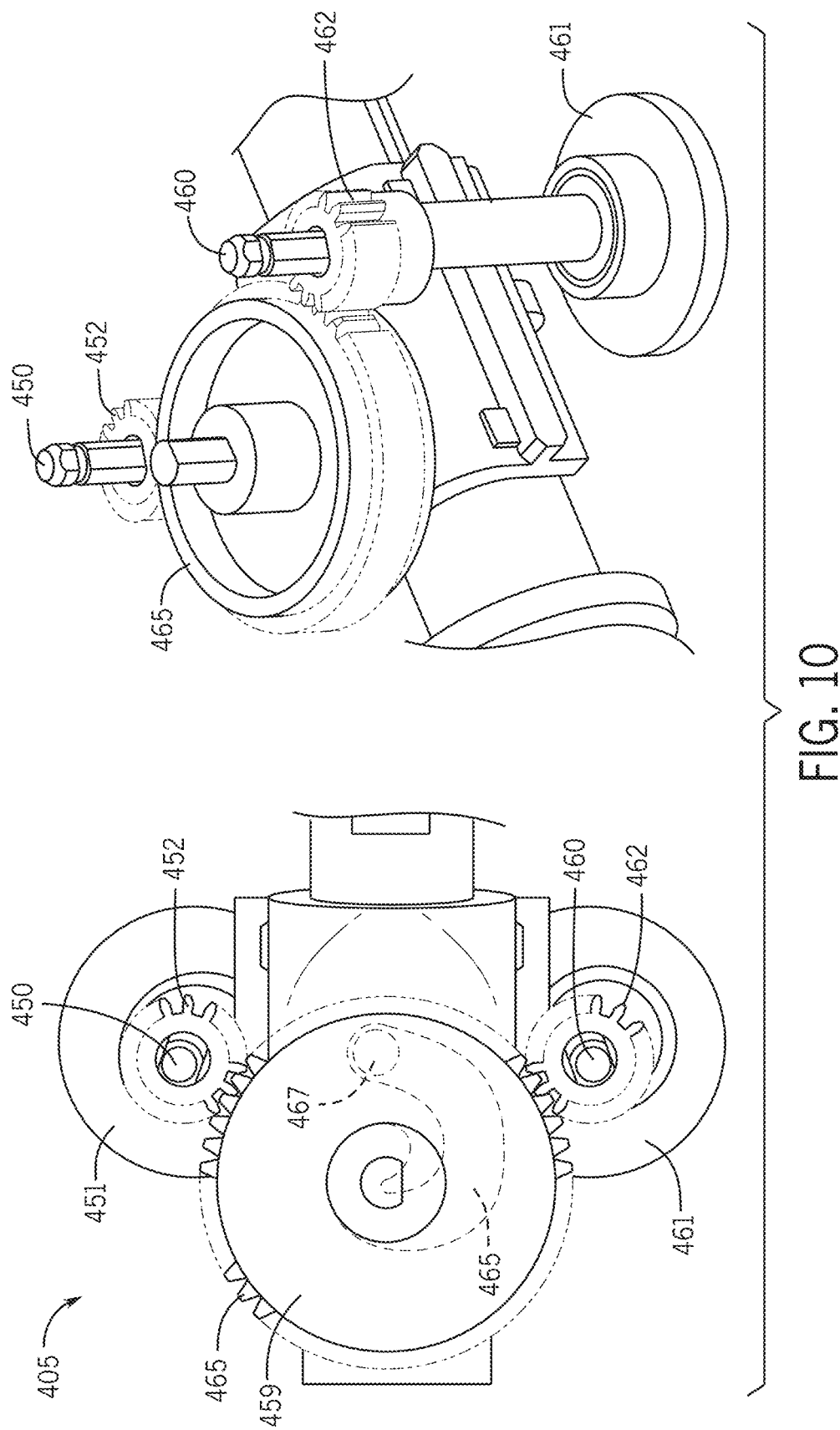
FIG. 10 illustrates a closure subsystem of the drive system for the surgical tool.

FIG. 10 illustrates a closure subsystem 405 of the drive system for the surgical tool. The closure subsystem 405 includes a left closure shaft 450 and a right closure shaft 460. The left closure shaft 450 is coupled to and driven by tool disk R5 (left closure input puck 451). The right closure shaft 460 is coupled to and driven by tool disk R6 (right closure input puck 461). A left drive gear 452 is coupled to the left closure shaft 450 and a right drive gear 462 is coupled to the right closure shaft 460. The left drive gear 452 and the right drive gear 462 cooperate to drive closure gear 465, which operates the closure joint.

A cam cam/yoke mechanism 459 translates the rotary input from the left closure input puck 451 and the right closure input puck 461 to a linear output. A variable mechanical advantage is provided by the cam/yoke mechanism 459 at a function of its angular position. For example, the cam/yoke mechanism 459 may include a push pull rod that distally includes a pin 467 that slides on a slot 468, creating the open and close jaw motion.

Figure 11:
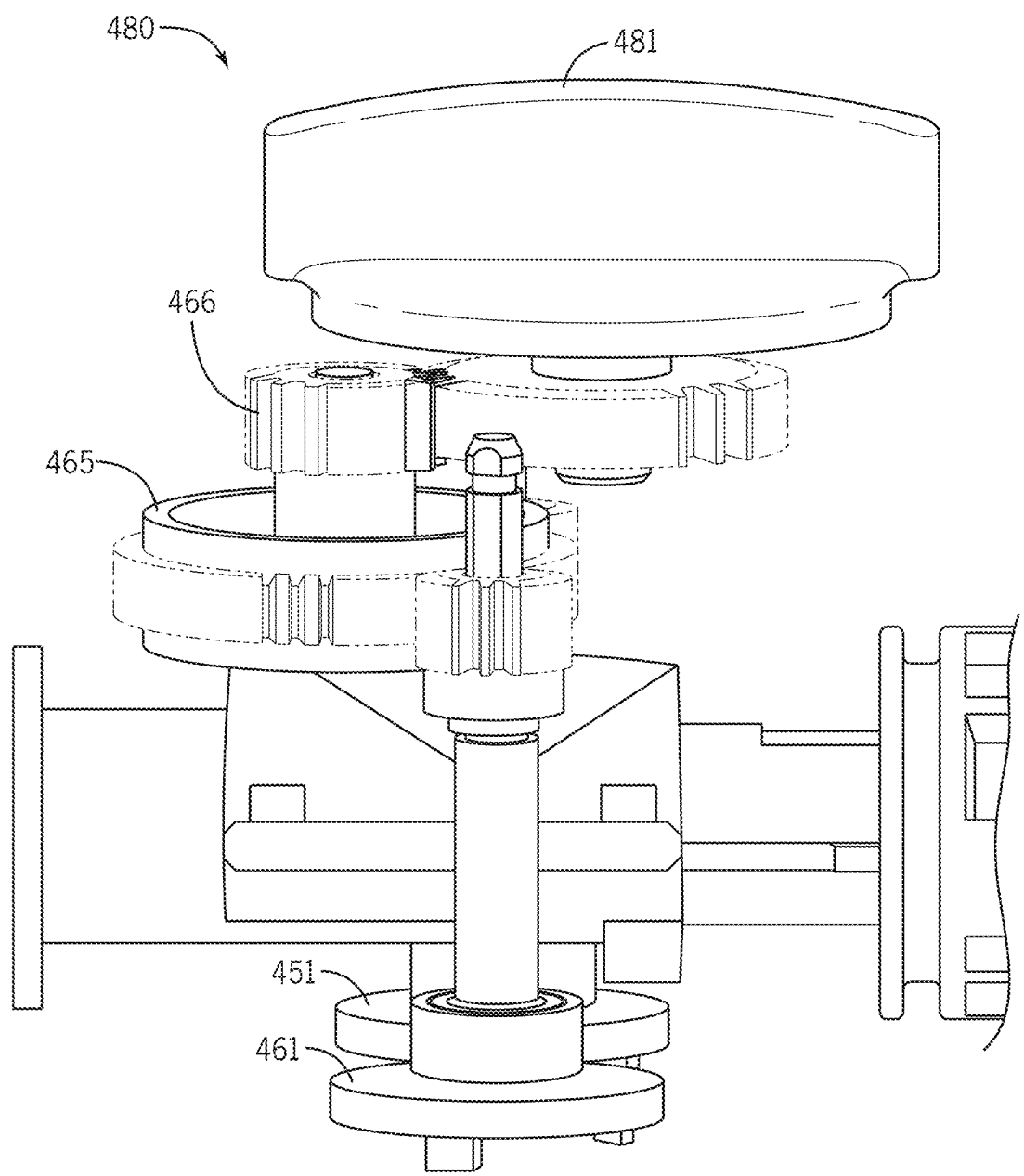
FIG. 11 illustrates a manual knob for the closure subsystem.

FIG. 11 illustrates a manual knob 481 for the closure subsystem 405. One or more coupling gears 466 couple the drive closure gear 465 to the manual know 481. The manual knob 481 includes a surface or handle for receiving a user's grip to rotate the manual knob 481, causing rotation of the left drive gear 452 and/or the right drive gear 462, to manually operate the closure joint.

Figure 12:
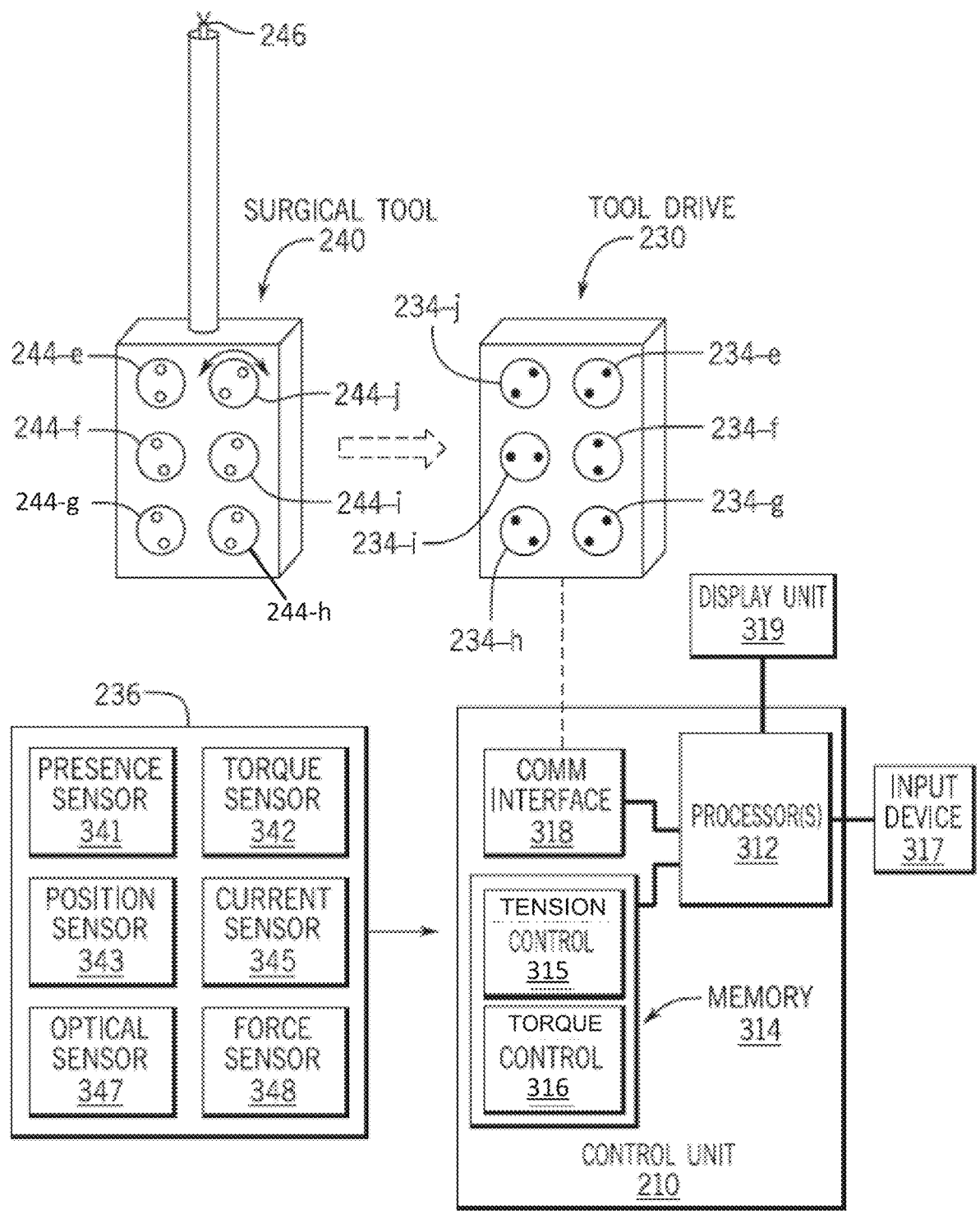
FIG. 12 illustrates a controller for the tool driver and/or surgical tool.

FIG. 12 illustrates an example of the surgical tool 240 that utilizes six tool disks, such as tool disks 244-*e, f, g, h, i, j,* arranged in a coplanar fashion on a mating surface of its housing. Any arrangement of tool disks 244-*e, f, g, h, i, j,* may correspond to tool disks R1-R6, in general, or specifically firing input puck 411, right articulation input puck 421, roll input puck 431, left articulation input puck 441, left closure input puck 451, and right closure input puck 461 described previously. Each tool disk contributes to at least a portion of the movement and/or activation of end effector 222. Upon detecting the attachment of surgical tool 240 with tool driver 230 (e.g., joining of mating surfaces of the respective housings), control unit 210 (or its processor 312 while executing instructions stored in memory 314 as) performs a process which determines that the corresponding drive disks, such as drive disks 234 *e, f, g, h, i, j*, are to be turned (a corresponding actuator 238 is activated) to perform the engagement process.

In some embodiments, the motor operating parameters monitored by the control unit 210 (via sensors 236) are interpreted to mean successful mechanical engagement of a tool disk with a drive disk. The control unit 210 is in communication with and receives sensor data from sensor 236 in an example sensor array including any combination of a presence sensor 341, a torque sensor 342, a position sensor 343, an electrical sensor 345, an optical sensor 347, and a force sensor 348. The sensor array may include separate sensors for different degrees of freedom of the surgical tool (e.g., closure joint, articulation joint, roll joint, or other operation of the surgical tool). That is, the sensor array, or one or more sensors thereof, may be repeated for multiple tool disks 244 in the tool driver 230.

The measurements may include measurements of torque applied by the actuator 238-*j* as measured by the torque sensor 342 or the force sensor 348, measurements of current by the electrical sensor 345 supplied to a motor of the actuator 238-*j* when attempting to drive the actuator to move at a certain velocity (e.g., where the sensor 236-*j* may include a current sensing resistor in series with a motor input drive terminal), measurements of electrical impedance by the electrical sensor 345 as seen into the input drive terminals of the motor of the actuator 238 when attempting to drive the motor to move at a certain velocity (e.g., where the sensor 236-*j* may also include a voltage sensing circuit to measure voltage of the motor input drive terminal), speed of the actuator 238-*j* (e.g., where the optical sensor 347 may include a position encoder on an output shaft of the actuator 238-*j* or on a drive shaft of the motor), as well as other parameters referred to here as motor operating parameters. The measurements may include presence data from the presence sensor 341, implied from any sensor in the sensor array 236, or determined from the interaction between the information storage unit 242 and the communication interface 232. The position sensor 343 is illustrated separately but may be implemented using a combination of the presence sensor 341, the torque sensor 342, the electrical sensor 345, the optical sensor 347, and the force sensor 348. In one example, additional sensors of the same type may be used for the position sensor 343.

While monitoring the one or more motor operating parameters of a particular actuator, when one or more of these parameters satisfies (e.g., meets or reaches) a predetermined, condition or threshold, the detection of such a situation can be interpreted by control unit 210 as a mechanical engagement event. Note that satisfying the predetermined condition may for example mean that the monitored operating parameter exhibits certain changes, as per the threshold, relative to an operating parameter of another motor that is part of the same actuator 238-*j* or that is part of another actuator 238-*i* which his being controlled by the control unit 210 simultaneously during the engagement detection process.

In some embodiments, detection of certain motor operating parameters during operation of the actuator 238-*j*, such as one or more of i) torque that satisfies (e.g., rises and reaches) a torque threshold, ii) motor current that satisfies (e.g., rises and reaches) a current threshold, iii) impedance that drops below an impedance threshold, iv) motor speed dropping below a motor velocity threshold, or a combination thereof, are used by control unit 210 to determine that mechanical engagement of tool disk 244-*j* to drive disk 234-*j* has occurred.

The control unit 210 including its programmed processor 312 may be integrated into the surgical robotic system 100 (FIG. 1) for example as a shared microprocessor and program memory within the control tower 130. Alternatively, the control unit 210 may be implemented in a remote computer such as in a different room than the operating room, or in a different building than the operating arena shown in FIG. 1. Furthermore, control unit 210 may also include, although not illustrated, user interface hardware (e.g., keyboard, touch-screen, microphones, speakers) that may enable manual control of the robotic arm and its attached surgical tool 240, a power device (e.g., a battery), as well as other components typically associated with electronic devices for controlling surgical robotic systems.

Memory 314 is coupled to one or more processors 312 (generically referred to here as a processor for simplicity) to store instructions for execution by the processor 312. In some embodiments, the memory is non-transitory, and may store one or more program modules, including a tension control algorithm 315 and a torque control algorithm 316, whose instructions configure the processor 312 to perform the tension and torque control algorithms 315 and 316 as described herein. In other words, the processor 312 may operate under the control of a program, routine, or the execution of instructions stored in the memory 314 as part of the tension control algorithm 315 and the torque control algorithm 316 to execute methods or processes in accordance with the aspects and features described herein. The memory 314 may include one or more settings, coefficient values, threshold values, tolerance values, calibration values for the surgical tool 240 and/or the tool driver 230. These values may be stored in memory 314 as a configuration file, table, or matrix. Some values in the configuration file may be provided by the user, some may be accessed or retrieved based on identifiers of the surgical tool 240 or tool driver 230, and others may be set by the control unit 210.

Figure 13:
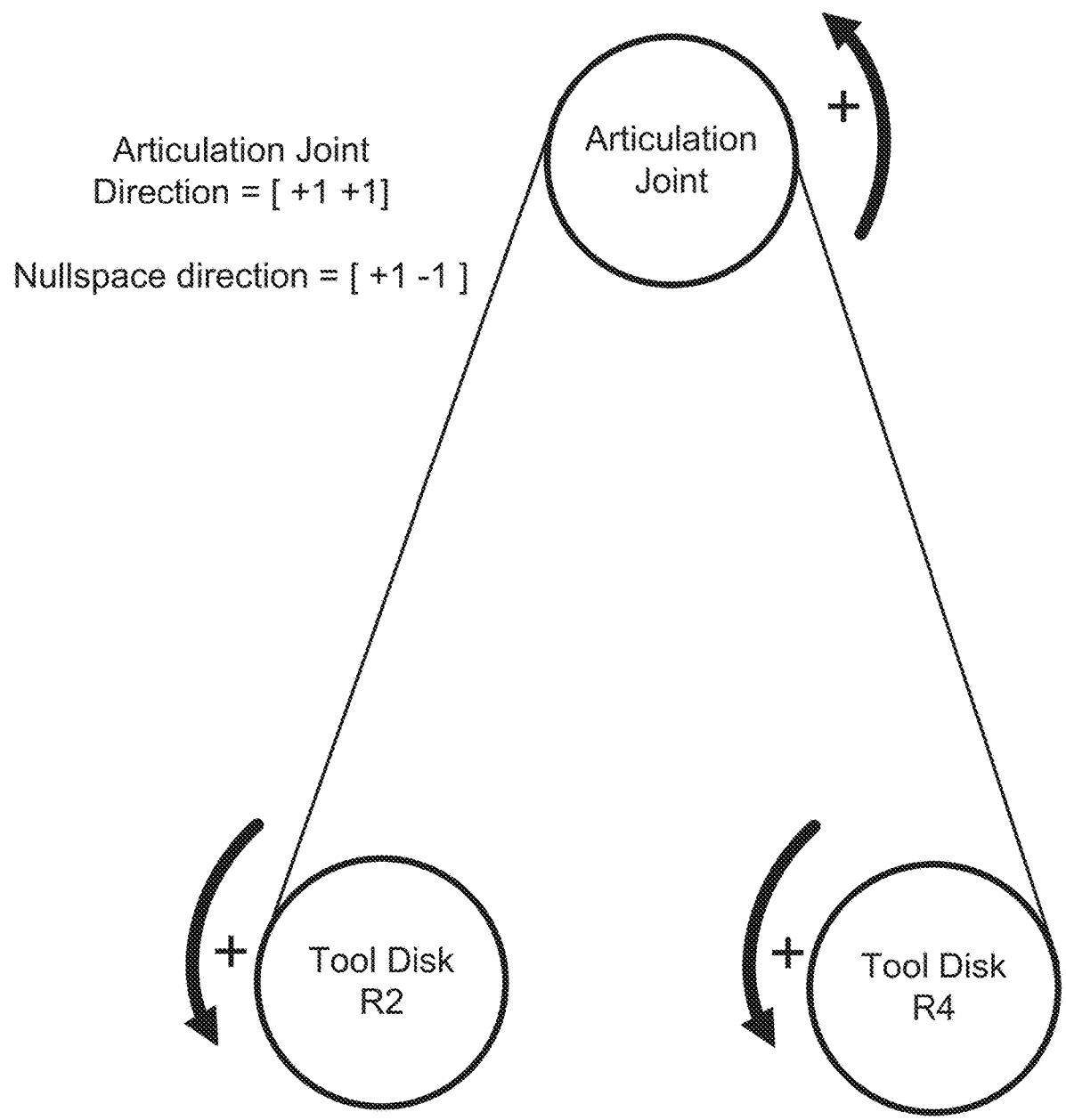
FIG. 13 illustrates a representation of the redundancy of the articulation joint.

FIG. 13 illustrates a representation of the redundancy of the articulation joint. The articulation joint for the surgical tool 240 is driven by two motors (e.g., the motors correspond to tool disks R2 and R4). The mechanical structure of the two motors driving one degree of freedom indicates that there is a one degree of freedom null space in the articulation joint control that is orthogonal to the articulation joint position space. In other words, the redundancy (R) is related to the number of motors/actuators (M) and the degrees of freedom of the joint (J) such that R=M−J. When R is a positive nonzero number, the joint control is said to have a redundancy, or the corresponding null space exists. When R=1, the joint control has one degree of redundancy and/or one degree of null space, when R=2 the joint has two degrees of redundancy, and/or two degrees of null space and so on. The control action done through this null space does not influence the articulation joint position. Therefore, this redundancy or null space could be used to achieve extra control objectives in some situations.

Continuing with the example of the articulation joint, the physical displacement of the articulation joint ($\theta_j$) is provided by Equation 1:

$$\theta_j = \frac{a + \frac{1}{2}(\theta_{m1} + \theta_{m2})}{b} \qquad \text{Eq. 1}$$

The relationship in Equation 1 is based on a first position ($\theta_{m1}$) for a first actuator (e.g., corresponding to tool disk R2) and a second actuator position ($\theta_{m2}$) for a second actuator (e.g., corresponding to tool disk R4), and at least one property constant including a first constant a and second constant b. The property constant may depend on the materials of the components, the relative dimensions of the components, or other factors.

The null space corresponding to the redundant DoF for the articulation wrist joint provides a relationship between the first movement of the two actuators and the second movement of the two actuators. For example, the relationship between the first movement of the two actuators [$\theta_{m1}^1$, $\theta_{m2}^1$] and the second movement of the two actuators [$\theta_{m1}^2$, $\theta_{m2}^2$] may be provided by Equation 2:

$$[\theta_{m1}^1, \theta_{m2}^1]^T = [\theta_{m1}^2, \theta_{m2}^2]^T + k[-1,1]^T \qquad \text{Eq. 2}$$

In Equation 2, the null space corresponding to the redundant DoF for the articulation wrist is described as a vector [1, −1] or [−1, 1]$^T$. Further, for the purpose of illustration, there may be a constraint that the joint position does not change ($\theta_j^1 = \theta_j^2$) but a null space can be calculated applicable to changes in the joint position as well. In the case of the surgical tool 240, the control system provides a redundant degree of freedom (DoF) for the end effector articulation joint of one DoF by driving the joint with two actuators.

Figure 14:
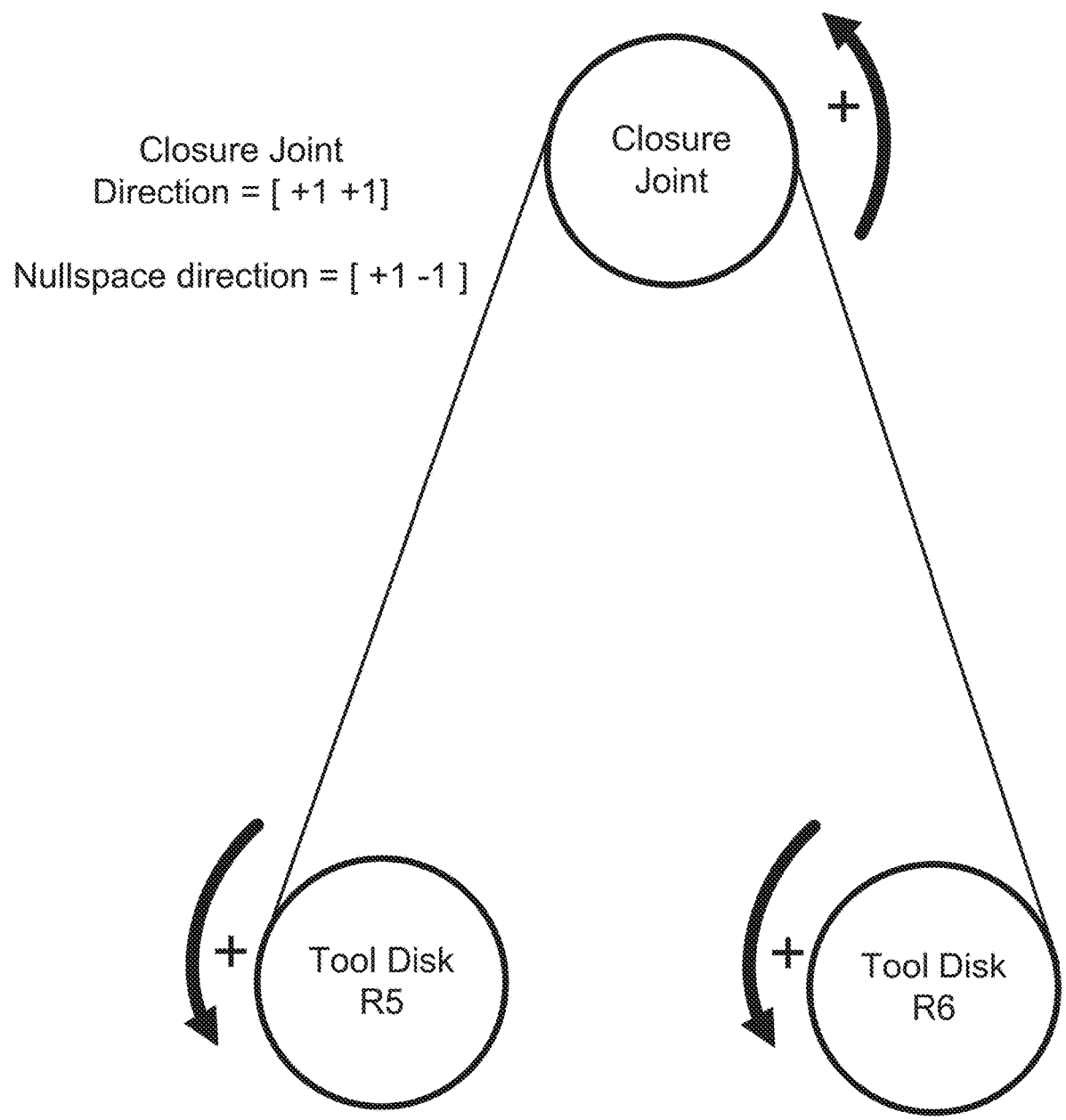
FIG. 14 illustrates a representation of the redundancy of the closure joint.

FIG. 14 illustrates a representation of the redundancy of the closure joint. In this embodiment, the closure joint uses rods and not cables. Rods apply forces in both the pulling and pushing directions as opposed to cables that apply force in only the pulling direction. FIG. 14 is for illustrative purposes. The closure joint for the surgical tool 240 is driven by two motors (e.g., the motors correspond to tool disks R5 and R6). There is also a mechanical structure of the two motors driving one degree of freedom indicates that the there is a one degree of freedom null space in the articulation joint control that is orthogonal to the articulation joint position space. In other words, the redundancy (R) is a positive nonzero number. The control action done through this null space does not influence the closure joint position. Therefore, this redundancy or null space could be used to achieve extra control objectives in some situations.

Continuing with the example of the closure joint, the physical displacement of the joint ($\theta_j$) is provided by Equation 3:

$$\theta_j = \sum_{i=0}^{n} a_i \left[ \frac{1}{2} * (\theta_{m1} + \theta_{m2}) \right]^i \qquad \text{Eq. 3}$$

The physical displacement of the joint ($\theta_j$) is based on a first position ($\theta_{m1}$) for a first actuator and a second actuator position ($\theta_{m2}$) for a second actuator, and $a_i$ is a constant coefficient from a tool calibration process. The constant coefficient may relate to the size, shape, or positions of the associated pucks (e.g., left closure input puck 451 and right closure input puck 461) such as the gear ratio or kinematic ration from inputs to joints. The constant coefficient may be related to the admittance or backlash between gears or other drive train components.

The null space corresponding to the redundant DoF for the closure joint provides a relationship between the first movement of the two actuators and the second movement of the two actuators. For example, the relationship between the first movement of the two actuators $[\theta_{m1}^1, \theta_{m2}^1]$ and the second movement of the two actuators $[\theta_{m1}^2, \theta_{m2}^2]$ may be provided by Equation 2:

$$[\theta_{m1}^1,\theta_{m2}^1]^T=[\theta_{m1}^2,\theta_{m2}^2]^T+k[1,-1]^T \qquad \text{Eq. 4}$$

In Equation 4, the null space corresponding to the redundant DoF for the closure joint is described as a vector $[1, -1]$ or $[1, -1]^T$. Further, for the purpose of illustration, there may be a constraint that the joint position does not change $(\theta_j^1=\theta_j^2)$ but a null space can be calculated applicable to changes in the joint position as well. In the case of the surgical tool 240, the control system provides a redundant degree of freedom (DoF) for the end effector joint of one DoF by driving the joint with two actuators.

Figure 15:
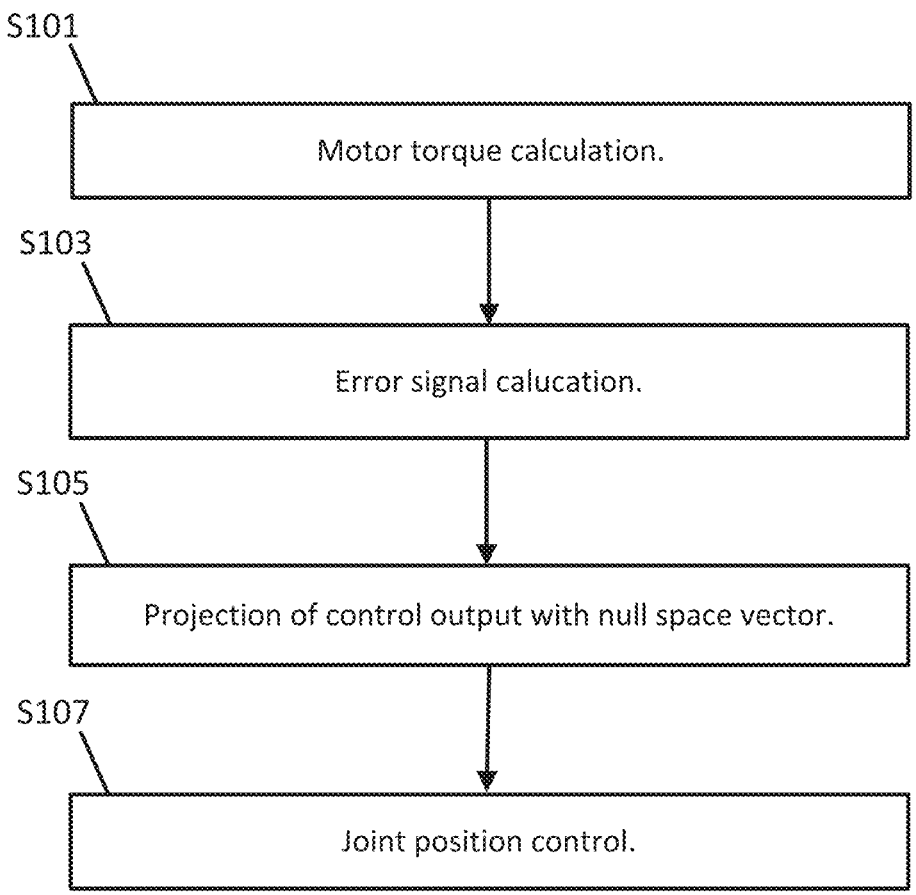
FIG. 15 illustrates an example control objective using the null space of the articulation subsystem.

FIG. 15 illustrates a procedure or technique that may be carried out by any of the systems described herein, for example, by a controller, such as the control unit 210. The process may be performed by a programmed processor (also referred to here as processor or controller), configured according to instructions stored in memory (e.g., the processor 312 and the memory 314 of FIG. 12, where the processor 312 is configured according to the instructions of the tension control algorithm 315 and the torque control algorithm 316). Each act in FIG. 15 may refer to a separate process that may have many steps. Additional, different, or fewer acts may be included.

At act S101, motor torque is determined or calculated. The motor torque may be measured at the motor, corresponding drive disk, or corresponding tool disk R1-6, which may include firing input puck 411, right articulation input puck 421, roll input puck 431, left articulation input puck 441, left closure input puck 451, and right closure input puck 461. The motor torque for the articulation joint may be determined based on torque measured at the right articulation input puck 421 and left articulation input puck 441. The motor torque for the closure joint may be determined based on torque measured at left closure input puck 451 and right closure input puck 461.

Any of the described sensors may generate sensor data used to determine motor torque. The torque may be directly measured by the associated torque sensor 342 or the force sensor 348 applied to the tool disk or motor. The motor torque may be indirectly measured from current sensed by the electrical sensor 345 supplied to a corresponding motor when attempting to drive the actuator to move at a certain velocity (e.g., a current sensing resistor in series with a motor input drive terminal). The motor torque may be indirectly measured by measurements of electrical impedance by the electrical sensor 345 as seen into the input drive terminals of the motor of the actuator 238 when attempting to drive the motor to move at a certain velocity. The motor torque may be indirectly measured by the speed of the tool disk or actuator (e.g., a position encoder on an output shaft of the actuator 238-$j$ or on a drive shaft of the motor).

At act S103, error signal calculations are performed. The error signal calculations are the feedback used to achieve the control objective for the particular joint. The error signal defines the control objective. For the articulation joint under control of the tension control algorithm 315, the control objective may be to maintain a minimum amount of tension torque on both of the motors along the null space direction in order to ensure the input gears (drive disks driven by the motors on the tool driver 230, for example, including tool disks R2 and R4) always engage with the output gears (driven disks for the articulation joint such as left articulation input puck 441 and the right articulation input puck 421). The motor's initial engaging direction determines which direction the initial motor tension is applied, with a torque reference $\tau_{min}$ to be a positive number, the controller specifies that $\tau_1<-\tau_{min}$ and $\tau_2>\tau_{min}$. In this example, $T_{min}$ is the minimum tension, $\tau_1$ is the first torque, and $\tau_2$ is the second torque. It should be noted that the positive and negative signs for $\tau_{min}$ are selected to match the null space direction provided above and in FIG. 13, but can be generalized for other cases.

In the example of the articulation joint under control of the tension control algorithm 315, the error signal (e) is calculated according to Equation 5:

$$e=\max(\tau_{min}+\tau_1,\tau_{min}-\tau_2) \qquad \text{Eq. 5}$$

In the example of the closure joint under control of the torque control algorithm 316, the closure joint should deliver a large amount of torque to be able to clamp the tissue in the most effective manner. This requires two/ motors, corresponding to the tool disks R5 and R6 and/or left closure input puck 451, and right closure input puck 461, to cooperate or work together to generate enough torque at the joint level. However, the mechanical structure cannot guarantee that and two motors work in cooperation during joint position control. To make sure the motors could work together to deliver enough torque at the joint level, the control objective for the closure joint may be to regulate the null space torque value to 0. To achieve this control goal, the control system applies one or more rules to calculate the error signal and apply output signal to general motor control.

For error signal calculation in the example of the closure joint under control of the torque control algorithm 316, in the example of the closure joint, the error signal (e) may be calculated according to Equation 6:

$$e=-\tau_1+\tau_2 \qquad \text{Eq. 6}$$

The error signal (e) is based on $\tau_1$ is the first torque, and $\tau_2$ is the second torque. In the example of the closure joint under control of the torque control algorithm 316, the error signal feedback that is minimized is the difference in motor torques associated with the two closure motors or the left closure input puck 451, and right closure input puck 461.

At act S105, the output of the controller using either the tension control algorithm 315 or the torque control algorithm 316 is projected onto the null space vector. The controller determines a projection of a control signal for the position displacement of the joint to a vector for the null space such that the projection represents the second control objective. For the example of the articulation joint and the tension control algorithm 315, the output signal is projected with the null space vector, which is an addition of the 2-dimension control signal to the articulation joint position control output. As the null space control amount does not influence the articulation joint position control, the minimum tension control for articulation motors is achieved while keep articulation joint position under control.

For the closure joint and the torque control algorithm 316, the second control objective is providing a certain torque at the closure jaw joint. The output signal is projected with the null space vector, which is an addition of the 2-dimension control signal to the closure joint position control output. As the null space control amount does not influence the closure joint position control, the control objective that the two closure motors always help each other to deliver joint level torque is achieved, while the closure joint position is also controlled as directed by the user input.

At act S107, the joint position control is performed using the output signal projected with the null space vector. The controller identifies or calculates an initial joint position or a change in joint position. The initial joint position may be determined from a user input. The initial joint position may also consider one or more supplemental positioning algorithms such as calibration, homing, engagement, or hardstop handling to determine an initial position for the joint that deviates from the user input.

The controller modifies the initial joint position to drive the joint according to a first movement specified by the user input and a second movement to effect the desired end effector movement while accomplishing the second control objective in the null space.

Figure 16:
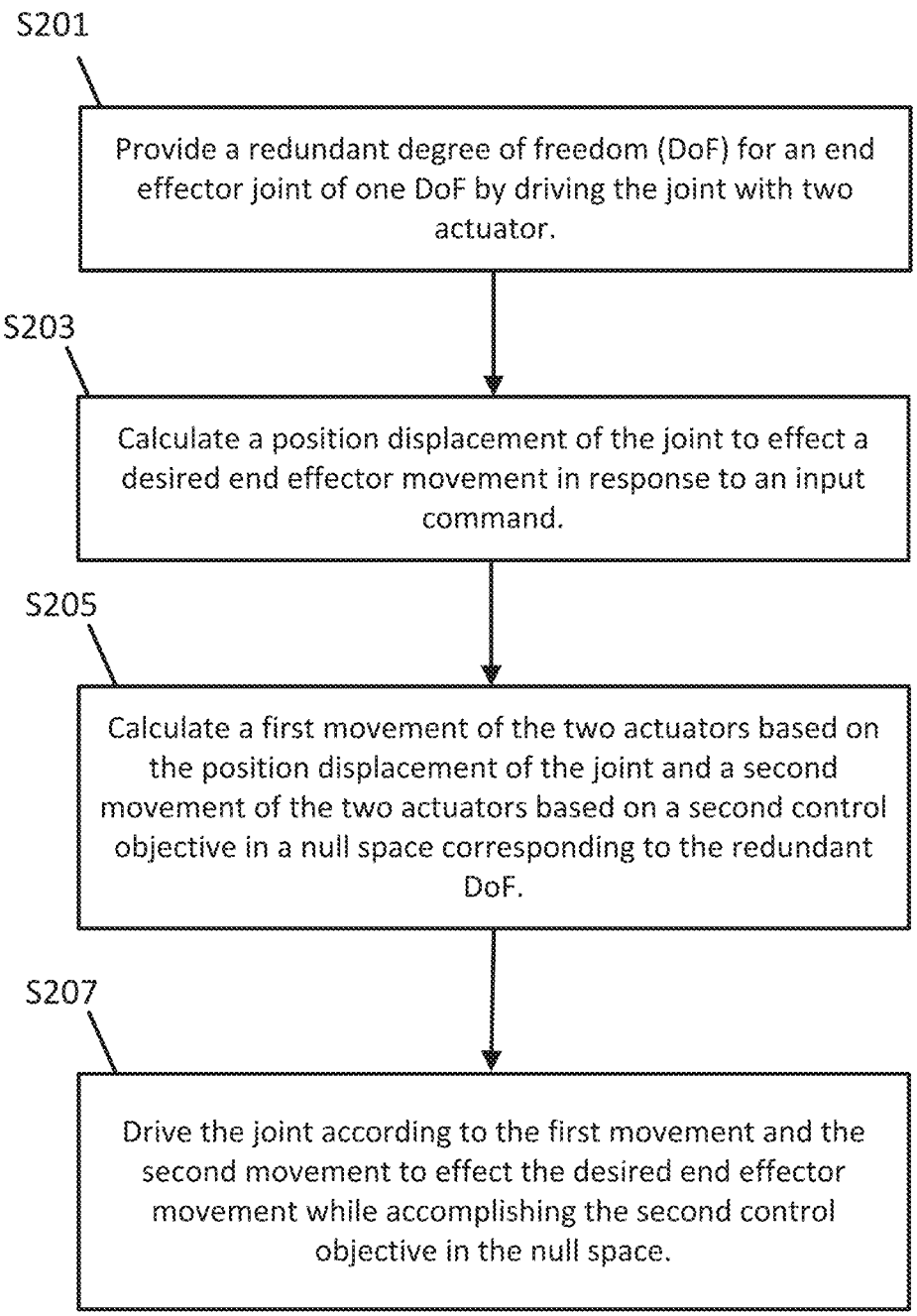
FIG. 16 illustrates a flow chart for an embodiment of the control system.

FIG. 16 illustrates a procedure or technique that may be carried out by any of the systems described herein, for example, by a controller, such as the control unit 210. The process may be performed by a programmed processor (also referred to here as processor or controller), configured according to instructions stored in memory (e.g., the processor 312 and the memory 314 of FIG. 12, where the processor 312 is configured according to the instructions of the tension control algorithm 315 and a torque control algorithm 316). Additional, different, or fewer acts than those in FIG. 16 may be performed.

At act S201, the processor 312 identifies a redundant DoF for an end effector joint of one DoF by driving the joint with two actuators. The redundant DoF may be provided by any surgical instrument having a joint that is coupled to more actuators or motors that the joint has DoF. In this case, at least one control DoF is redundant because it is in excess of the actual DoFs of the joint. The redundant DoF means that the control space solution as more than 1 dimension, which allows for at least one additional control objective to be perform simultaneously with position control for the joint.

At act S203, the processor 312 calculates a position displacement of the joint to effect a desired end effector movement in response to an input command. The input command may be received via a local or remote user input (e.g., joystick, touch control, wearable device, or other user input device communicating via console computer system.) Alternatively, the control unit 210 may generate autonomous commands or controls (e.g., received form a trained surgical machine learning model that is being executed by the control unit 210 or by the console computer system), or a combination thereof. The commands dictate the movement of end effector 222.

For example, the processor 312 may generate one or more actuation commands for movement of the tool disks through operation of the corresponding motor or motors. The command may be a new position of the motor (e.g., angular position) or a directional instruction (e.g., clockwise or counterclockwise) by a certain amount.

At act S205, the processor 312 calculates a first movement of the two actuators based on the position displacement of the joint and a second movement of the two actuators based on a second control objective in a null space corresponding to the redundant DoF. The first movement is based on the position displacement of the joint to effect the desired end effector movement in response to the input command in act S203. The first movement may be calculated from a current position of the two actuators and the desired end effector movement.

The second movement takes into consideration the second control objective. The second control objective may be different for different joints. For the articulation joint, the tension control algorithm 315, may include one or more control system with a feedback loop to maintain a minimum amount of tension torque on both of the motors along the null space direction so that the applicable drive disks (e.g., tool disks R2 and R4) that drive the left articulation input puck 441 and the right articulation input puck 421. The feedback loop may provide an error signal for the difference between the torque and the motors and a minimum threshold. The output of the control system may be the second movement for the joint to realize the second objective.

For the closure joint, the torque control algorithm 316 may include one or more control system with a feedback loop to maintain an even distribution of torque on the motors along the null space direction to maintain a predetermined total amount of torque from the tool disks R5 and R6 and/or left closure input puck 451, and right closure input puck 461. The feedback loop may provide an error signal that is minimized is the difference in motor torques. The output of the control system may be the second movement for the joint to realize the second objective.

At act S207, the processor 312 generates one or more joint commands to drive the joint according to the first movement and the second movement to effect the desired end effector movement while accomplishing the second control objective in the null space. That is the first movement corresponding to the position displacement calculated in act S203 is adjusted based on the second movement for the second control objective calculated in act S205. The joint command includes a joint position or change in joint position that is provided to the applicable motors or actuators. The joint command may include a first command for the first motor associated with the joint and a second command for the second motor associated with the joint. In the case of the articulation joint, the joint command instructs the motors to move the tool disks R2 and R4 that drive the left articulation input puck 441 and the right articulation input puck 421. In the case of the closure joint, the joint commands instructs the motors to move the tool disks R5 and R6 that drive the left closure input puck 451, and right closure input puck 461.

Herein, the phrase "coupled with" is defined to mean directly connected to or indirectly connected through one or more intermediate components. Such intermediate components may include both hardware- and software-based components. Further, to clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The disclosed mechanisms may be implemented at any logical and/or physical point(s), or combinations thereof, at which the relevant information/data (e.g., message traffic and responses thereto) may be monitored or flows or is otherwise accessible or measurable, including one or more gateway devices, modems, computers or terminals of one or more market participants, e.g., client computers, etc.

One skilled in the art will appreciate that one or more modules described herein may be implemented using, among other things, a tangible computer-readable medium comprising computer-executable instructions (e.g., executable software code). Alternatively, modules may be implemented as software code, firmware code, specifically configured hardware or processors, and/or a combination of the aforementioned.

The operations of computer devices and systems shown in FIGS. 1-25 may be controlled by computer-executable instructions stored on a non-transitory computer-readable medium. For example, the exemplary computer device or control unit 210 may store computer-executable instructions, generate electronic messages, extracting information from the electronic messages, executing actions relating to the electronic messages, and/or calculating values from the electronic messages to facilitate any of the algorithms or acts described herein. Numerous additional servers, computers, handheld devices, personal digital assistants, telephones, and other devices may also be connected to control unit 210.

As illustrated in FIG. 12, the computer system may include a processor 312 implemented by a central processing unit (CPU), a graphics processing unit (GPU), or both. The processor 312 may be a component in a variety of systems. For example, the processor 312 may be part of a standard personal computer or a workstation. The processor 312 may be one or more general processors, digital signal processors, specifically configured processors, application specific integrated circuits, field programmable gate arrays, servers, networks, digital circuits, analog circuits, combinations thereof, or other now known or later developed devices for analyzing and processing data. The processor 312 may implement a software program, such as code generated manually (i.e., programmed).

The computer system includes memory 314 that can communicate via a bus. The memory 314 may be a main memory, a static memory, or a dynamic memory. The memory 314 may include, but is not limited to, computer-readable storage media such as various types of volatile and non-volatile storage media, including but not limited to random-access memory, read-only memory, programmable read-only memory, electrically programmable read-only memory, electrically erasable read-only memory, flash memory, magnetic tape or disk, optical media and the like. In one embodiment, the memory 314 includes a cache or random-access memory for the processor 312. In alternative embodiments, the memory 314 is separate from the processor 312, such as a cache memory of a processor, the system memory, or other memory. The memory 314 may be an external storage device or database for storing data. Examples include a hard drive, compact disk ("CD"), digital video disc ("DVD"), memory card, memory stick, floppy disk, universal serial bus ("USB") memory device, or any other device operative to store data. The memory 314 is operable to store instructions executable by the processor 312. The functions, acts or tasks illustrated in the figures or described herein may be performed by the programmed processor 312 executing the instructions stored in the memory 314. The functions, acts or tasks are independent of the particular type of instructions set, storage media, processor or processing strategy and may be performed by software, hardware, integrated circuits, firmware, micro-code, and the like, operating alone or in combination. Likewise, processing strategies may include multiprocessing, multitasking, parallel processing, and the like.

The computer system may further include a display unit 319, such as a liquid crystal display (LCD), an organic light emitting diode (OLED), a flat panel display, a solid-state display, a cathode ray tube (CRT), a projector, a printer or other now known or later developed display device for outputting determined information. The display 319 may act as an interface for the user to see the functioning of the processor 312, or specifically as an interface with the instructions stored in the memory 314 or elsewhere in the control unit 210.

Additionally, the computer system may include an input device 317 configured to allow a user to interact with any of the components of system. The input device 317 may be a number pad, a keyboard, or a cursor control device, such as a mouse, or a joystick, touch screen display, remote control, or any other device operative to interact with the control unit 210.

The present disclosure contemplates a computer-readable medium that includes instructions or receives and executes instructions responsive to a signal, so that a device connected to a network can communicate voice, video, audio, images, or any other data over the network. Further, the instructions may be transmitted or received over the network via a communication interface 318. The communication interface 318 may be a part of the processor 312 or may be a separate component. The communication interface 218 may be a physical connection in hardware. The communication interface 318 is configured to connect with a network, external media, the display unit 319, or any other components in the system, or combinations thereof. The connection with the network may be a physical connection, such as a wired Ethernet connection or may be established wirelessly. Likewise, the additional connections with other components of the system may be physical connections or may be established wirelessly.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the described embodiments should not be understood as requiring such separation in all embodiments, and it should be understood that the described program components and systems can generally be integrated together in a single software product or packaged into multiple software products.

What is claimed is:

1. A robotic method comprising:
   providing a redundant degree of freedom (DoF) for an end effector joint of one DoF by driving the joint with two actuators;
   calculating a position displacement of the joint to effect a desired end effector movement in response to an input command;
   calculating a first movement of the two actuators based on the position displacement of the joint and a second movement of the two actuators based on a second control objective in a null space corresponding to the redundant DoF; and
   driving the joint according to the first movement and the second movement to effect the desired end effector movement while accomplishing the second control objective in the null space,
   wherein the joint is an articulation wrist coupled to two actuators through cables,
   wherein the second control objective is maintaining a minimum tension on the cables, and
   wherein the minimum tension is maintained by a control system having an error signal based on a first torque of one of the two actuators and a second torque of the other of the two actuators.

2. The robotic method of claim 1, further comprising: calculating the error signal (e) according to:

$$e = \max(\tau_{min} + \tau_1, \tau_{min} - \tau_2),$$

wherein $\tau_{min}$ is the minimum tension, $\tau_1$ is the first torque, and $\tau_2$ is the second torque.

3. The robotic method of claim 1, wherein the null space corresponding to the redundant DoF for the articulation wrist is described as a vector $[-1, 1]$ or $[-1, 1]^T$.

4. The robotic method of claim 3, wherein the null space corresponding to the redundant DoF for the articulation wrist provides a relationship between the first movement of the two actuators and the second movement of the two actuators.

5. The robotic method of claim 3, wherein a relationship between the first movement of the two actuators $[\theta_{m1}^1, \theta_{m2}^1]$ and the second movement of the two actuators $[\theta_{m1}^2, \theta_{m2}^2]$ includes $[\theta_{m1}^1, \theta_{m2}^1]^T = [\theta_{m1}^2, \theta_{m2}^2]^T + [-1, 1]^T$, where k is a constant number.

6. The robotic method of claim 1, wherein a physical displacement of the joint ($\theta_j$) is provided by:

$$\theta_j = \frac{a + \frac{1}{2}(\theta_{m1} + \theta_{m2})}{b},$$

based on a first position ($\theta_{m1}$) for a first actuator and a second actuator position ($\theta_{m2}$) for a second actuator, and at least one property constant includes first constant a and second constant b.

7. A robotic method comprising:
   providing a redundant degree of freedom (DoF) for an end effector joint of one DoF by driving the joint with two actuators;
   calculating a position displacement of the joint to effect a desired end effector movement in response to an input command;
   calculating a first movement of the two actuators based on the position displacement of the joint and a second movement of the two actuators based on a second control objective in a null space corresponding to the redundant DoF;
   driving the joint according to the first movement and the second movement to effect the desired end effector movement while accomplishing the second control objective in the null space,
   wherein the joint is a closure jaw joint of the end effector, wherein the second control objective is providing a certain torque at the closure jaw joint, wherein the certain torque is maintained by a control system having an error signal based on a first torque of one of the two actuators and a second torque of the other of the two actuators.

8. The robotic method of claim 7, further comprising: calculating the error signal (e) according to:

$$e = -\tau_1 + \tau_2,$$

wherein $\tau_1$ is the first torque, and $\tau_2$ is the second torque.

9. The robotic method of claim 7, wherein a physical displacement of the joint ($\theta_j$) is provided by:

$$\theta_j = \sum_{i=0}^{n} a_i \left[ \frac{1}{2} * (\theta_{m1} + \theta_{m2}) \right]^i,$$

based on a first position ($\theta_{m1}$) for a first actuator and a second actuator position ($\theta_{m2}$) for a second actuator, and $a_i$ is a constant coefficient from a tool calibration process.

10. The robotic method of claim 7, wherein the null space corresponding to the redundant DoF for the closure jaw joint is described as a vector $[1, -1]$ or $[1, -1]^T$.

11. The robotic method of claim 10, wherein the null space corresponding to the redundant DoF for the closure jaw joint provides a relationship between the first movement of the two actuators and the second movement of the two actuators.

12. The robotic method of claim 11, wherein the relationship between the first movement of the two actuators $[\theta_{m1}^1, \theta_{m2}^1]$ and the second movement of the two actuators $[\theta_{m1}^2, \theta_{m2}^2]$ includes $[\theta_{m1}^1, \theta_{m2}^1]^T = [\theta_{m1}^2, \theta_{m2}^2]^T + k[1, -1]^T$, where k is a constant number.

13. The robotic method of claim 1, further comprising: determining a projection of a control signal for the position displacement of the joint to a vector for the null space, wherein the projection represents the second control objective.

14. An apparatus to provide a control objective using a null space of a redundant degree of freedom of a surgical tool, the apparatus comprising:

a tool driver including a plurality of actuators providing a redundant degree of freedom (DoF) for an end effector joint of one DoF; and one or more processors configured to:
provide a redundant degree of freedom (DoF) for an end effector joint of one DoF by driving the joint with two actuators;
calculate a position displacement of the joint to effect a desired end effector movement in response to an input command;
calculate a first movement of the two actuators based on the position displacement of the joint and a second movement of the two actuators based on a second control objective in a null space corresponding to the redundant DoF; and
generate a joint command for the joint according to the first movement and the second movement to effect the desired end effector movement while accomplishing the second control objective in the null space,
wherein the joint is an articulation wrist coupled to two actuators through cables,
wherein the second control objective is maintaining a minimum tension on the cables, and
wherein the minimum tension is maintained by a control system having an error signal based on a first torque of one of the two actuators and a second torque of the other of the two actuators.

15. The apparatus of claim 14, wherein the error signal (e) is calculated according to:

$e = \max(\tau_{min} + \tau_1, \tau_{min} - \tau_2)$, wherein $\tau_{min}$ is the minimum tension, $\tau_1$ is the first torque, and $\tau_2$ is the second torque.

16. The apparatus of claim 14, wherein the null space corresponding to the redundant DoF for the articulation wrist is described as a vector $[-1, 1]$ or $[-1, 1]^T$.

17. The apparatus of claim 14, wherein the null space corresponding to the redundant DoF for the articulation wrist provides a relationship between the first movement of the two actuators and the second movement of the two actuators.

18. The apparatus of claim 14, wherein a relationship between the first movement of the two actuators $[\theta_{m1}^1, \theta_{m2}^1]$ and the second movement of the two actuators $[\theta_{m1}^2, \theta_{m2}^2]$ includes $[\theta_{m1}^1, \theta_{m2}^1]^T = [\theta_{m1}^2 \theta_{m2}^2]^T + k[-1, 1]^T$, where k is a constant number.

19. A non-transitory computer readable medium including instructions to cause one or more processors to perform:
identifying a redundant degree of freedom (DoF) for an end effector joint of one DoF by driving the joint with a plurality of actuators;
calculating a position displacement of the joint to effect a desired end effector movement in response to an input command;
calculating a first movement of the plurality of actuators based on the position displacement of the joint and a second movement of the plurality of actuators based on a second control objective in a null space corresponding to the redundant DoF; and
driving the joint according to the first movement and the second movement to effect the desired end effector movement while accomplishing the second control objective in the null space,
wherein the joint is a closure jaw joint of the end effector, wherein the second control objective is providing a certain torque at the closure jaw joint, wherein the certain torque is maintained by a control system having an error signal based on a first torque of one of the plurality of actuators and a second torque of another of the plurality of actuators.

* * * * *